(12) United States Patent
Ishimaru

(10) Patent No.: US 11,402,270 B2
(45) Date of Patent: Aug. 2, 2022

(54) SPECTRAL MEASUREMENT DEVICE AND SPECTRAL MEASUREMENT METHOD

(71) Applicant: NATIONAL UNIVERSITY CORPORATION KAGAWA UNIVERSITY, Takamatsu (JP)

(72) Inventor: Ichiro Ishimaru, Takamatsu (JP)

(73) Assignee: NATIONAL UNIVERSITY CORPORATION KAGAWA UNIVERSITY, Takamatsu (JP)

( * ) Notice: Subject to any disclaimer, the term of this patent is extended or adjusted under 35 U.S.C. 154(b) by 0 days.

(21) Appl. No.: 17/121,100

(22) PCT Filed: Jun. 13, 2019

(86) PCT No.: PCT/JP2019/023519
§ 371 (c)(1),
(2) Date: Dec. 14, 2020

(87) PCT Pub. No.: WO2019/240227
PCT Pub. Date: Dec. 19, 2019

(65) Prior Publication Data
US 2021/0310869 A1    Oct. 7, 2021

(30) Foreign Application Priority Data

Jun. 13, 2018  (JP) ............................ JP2018-112764
Jul. 30, 2018  (JP) ............................ JP2018-142832

(51) Int. Cl.
*G01J 3/453*    (2006.01)
*G01J 3/02*     (2006.01)
(Continued)

(52) U.S. Cl.
CPC .......... *G01J 3/4531* (2013.01); *G01J 3/0208* (2013.01); *G01N 21/255* (2013.01); *G01J 3/0256* (2013.01); *G01N 2021/3595* (2013.01)

(58) Field of Classification Search
None
See application file for complete search history.

(56) References Cited

U.S. PATENT DOCUMENTS 1,339,235 A  * 5/1920 Harold ..................... G01C 3/12
                                                    356/16
5,035,486 A  * 7/1991 Inokuchi .............. G02B 3/0062
                                                    359/625

(Continued)

FOREIGN PATENT DOCUMENTS

JP        2008-309706 A      12/2008
JP         2012-58068 A       3/2012
JP        2012-181060 A       9/2012

OTHER PUBLICATIONS

Jul. 30, 2019 International Search Report issued in International Patent Application No. PCT/JP2019/023519.

(Continued)

*Primary Examiner* — Shawn Decenzo
(74) *Attorney, Agent, or Firm* — Oliff PLC

(57) ABSTRACT

A combining light emitted from a measurement point of an object to be measured into one parallel light beam by combining optical system; dividing, by phase shifter, parallel light beam emitted from combining optical system into first and second light beam, emitting first and second light beam toward light-receiving face while providing an optical path length difference between the first and second light beam, and causing the first and second light beam to planarly enter the light-receiving face so that at least a part of an incident region of first light beam on the light-receiving face and at least a part of an incident region of second light beam overlap with each other; and obtaining an interferogram at measurement point based on intensity distribution of light in a region where an incident region of the first and second light beam on light-receiving face overlap, and acquiring spectrum by Fourier-transforming interferogram.

16 Claims, 14 Drawing Sheets

(51) Int. Cl.
  *G01N 21/25* (2006.01)
  *G01N 21/35* (2014.01)

(56) References Cited

U.S. PATENT DOCUMENTS

| | | | | |
|---|---|---|---|---|
| 11,181,469 | B2* | 11/2021 | Murayama | G01J 3/2803 |
| 2006/0114542 | A1* | 6/2006 | Bloom | G02B 26/06 |
| | | | | 359/276 |
| 2011/0317262 | A1* | 12/2011 | Hsu | H04N 13/305 |
| | | | | 359/463 |
| 2013/0215428 | A1* | 8/2013 | Ishimaru | A61B 5/1455 |
| | | | | 356/451 |
| 2015/0198483 | A1* | 7/2015 | Ishimaru | G01J 3/0208 |
| | | | | 356/451 |
| 2021/0191110 | A1* | 6/2021 | Holler | G02B 26/108 |

OTHER PUBLICATIONS

Jun. 25, 2021 Search Report issued in European Patent Application No. 19820128.7.
Junttila, Marja-Leena, "Stationary Fourier-transform spectrometer" Applied Optics 31 (1992) Jul. 20, No. 21, New York pp. 4106-4112.
Jul. 30, 2019 Written Opinion issued in International Patent Application No. PCT/JP2019/023519.
May 31, 2022 Office Action issued in Japanese Patent Application No. 2018-112764.

* cited by examiner

SPECTRAL MEASUREMENT DEVICE AND SPECTRAL MEASUREMENT METHOD

TECHNICAL FIELD

The present invention relates to a technique for qualitatively or quantitatively measuring physical properties of an object to be measured by utilizing spectral characteristics of the object to be measured.

BACKGROUND ART

In various diseases such as diabetes and hyperlipidemia, controlling biological components such as glucose and cholesterol included in blood is important to prevent and treat the diseases. To measure biological components in blood, blood needs to be drawn. However, in order to draw blood, troublesome treatments, such as sterilization of a blood drawing area and disposal of the blood collection tools, are necessary, so that, frequent blood drawing for the measurement of biological components for preventive purposes is apt to be averted. Therefore, a non-invasive measurement device that can measure biological components without drawing blood is proposed.

For example, Patent Literature 1 and Patent Literature 2 describe a spectral measurement device in which light is cast to a biological testing area, whereby biological components are detected using spectral characteristics of light (object light) emitted from the biological components inside of the testing area, and the biological components are qualitatively and quantitatively measured from the spectral characteristics.

In the device disclosed in Patent Literature 1, object light, including transmitted light, diffused light, and scattered light, generated from each bright point that optically forms the biological components is combined into one parallel light beam (object beam) by an objective lens, and then introduced to a phase shifter composed of a fixed mirror and a movable mirror. The object beams reflected by each of the fixed mirror and the movable mirror pass through an imaging lens, and then focused on an imaging plane to interfere. The fixed mirror and the movable mirror are arranged side by side and have mutually parallel reflection faces. The movable mirror is moved in the direction normal to the reflection face by a piezo element or the like, and a difference in the optical path length is provided between the object beams reflected by the fixed mirror and the object beams reflected by the movable mirror according to the moving distance of the movable mirror. Thus, when the optical path length difference between the two object beams changes with the movement of the movable mirror, the intensity of the interference light on the imaging plane changes, and a so-called interferogram is created. Then, the interferogram is Fourier-transformed to obtain the spectral characteristics (spectrum) of the object light.

In the device disclosed in Patent Literature 2, the phase shifter includes two mirrors (a reference mirror and an inclined mirror) arranged side by side and having different inclinations of the reflection faces. In this device, object beams generated from each bright point and combined by an objective lens is introduced to the reference mirror and the inclined mirror, and reflected by the reflection face of each mirror. The light reflected by the reference mirror (reference reflected light) and the light reflected by the inclined mirror (inclined reflected light) are focused by an imaging lens on the same straight line extending in a direction different from either of the optical axes of the reference reflected light and the inclined reflected light to form a linear interference image. Since the inclination of the reflection face of the reference mirror and that of the inclined mirror are different, a continuous optical path length difference between the reference reflected light and the inclined reflected light is generated corresponding to the difference in angles between the optical axis of the object beams and the respective reflection faces of the reference mirror and the inclined mirror. Accordingly, an interferogram is acquired by measuring a change in light intensity along the linear interference image. The spectral characteristics of the object light can be obtained by Fourier-transforming the interferogram.

CITATION LIST

Patent Literature

Patent Literature 1: JP 2008-309706 A
Patent Literature 2: JP 2012-058068 A

SUMMARY OF INVENTION

Technical Problem

Since the spectral characteristics of the object light indicate the properties of the biological components, the biological components can be measured qualitatively and quantitatively in a non-invasive manner by using the device described in Patent Literatures 1 and 2. However, in order for the device described in Patent Literature 1 to obtain accurate spectral characteristics, it is necessary to move the movable mirror with high accuracy and high motion straightness, which requires an expensive drive mechanism such as a high-accuracy piezo stage. Also, the size of the device is increased due to the drive mechanism of the movable mirror.

On the other hand, the device disclosed in Patent Literature 2 does not require a mechanism for moving a mirror, and hence, the problem as seen in the device disclosed in Patent Literature 1 does not occur. However, in the device described in Patent Literature 2, one linear interference image is formed from the object light generated from each bright point, and the spectral characteristics are obtained by detecting a change in light intensity along the interference image. Accordingly, in order to enhance the wavelength resolution, it is necessary to increase the number of pixels of the element that detects the change in light intensity in the interference image. In order to do so, it is necessary to increase the size of the light-receiving face, the phase shifter, the objective lens, and the like of the detector, which also increases the size of the device.

A problem to be solved by the present invention is to measure accurate and high wavelength resolution spectral characteristics without increasing the size of the device.

Solution to Problem

A spectral measurement device according to the present invention made to solve the above problem includes:

a) a combining optical system configured to combine light emitted from a measurement point of an object to be measured into one single parallel light beam;

b) a detector having a light-receiving face and configured to detect an intensity distribution of light on the light-receiving face;

c) a phase shifter configured to divide a parallel light beam combined in the combining optical system into a first light beam and a second light beam, configured to emit the first light beam and the second light beam toward the light-receiving face while providing an optical path length difference between the first light beam and the second light beam, and configured to cause the first light beam and the second light beam to planarly enter the light-receiving face so that at least a part of an incident region of the first light beam on the light-receiving face and at least a part of an incident region of the second light beam overlap with each other; and d) a processing unit configured to obtain an interferogram at the measurement point based on an intensity distribution of light in the region where the incident region of the first light beam and the incident region of the second light beam on the light-receiving face overlap, and configured to acquire a spectrum by Fourier-transforming the interferogram.

The combining optical system may be composed of one objective lens (collimator lens). Otherwise it may be composed of a condenser lens and an objective lens (collimator lens), or it may be composed of a condenser lens and an objective lens as well as a pinhole arranged at the common focal position of the both lenses. A concave mirror can also be used as the combining optical system.

In the spectral measurement device having the above-described configuration, the parallel light beam combined in the combining optical system is emitted from the combining optical system, divided into a first light beam and a second light beam by the phase shifter, and then planarly enters the light-receiving face of the detector in a state where at least a part of the incident region of the first light beam on the light-receiving face and the incident region of the second light beam overlap. At this time, since a predetermined optical path length difference is provided between the first light beam and the second light beam, an interference image of the first light beam and the second light beam is formed in the region (overlap region) where the incident regions of both light beams overlap. Accordingly, by detecting the intensity distribution of the light in the overlap region, the intensity distribution of the interference image, i.e., the interferogram of the measurement point is acquired, and it is possible to acquire the spectral characteristics of the measurement point by Fourier-transforming the interferogram.

In the above spectral measurement device, the phase shifter has a first planar reflection face and a second planar reflection face arranged side by side so that the parallel light beam enters from an oblique direction, and it is preferable that the first reflection face and the second reflection face are configured so that an incident angle of the parallel light beam with respect to the first reflection face and an incident angle of the parallel light beam with respect to the second reflection face are different from each other, and an incident face of the parallel light beam with respect to the first reflection face and an incident face of the parallel light beam with respect to the second reflection face are different from each other.

In this configuration, the parallel light beam having been emitted from the combining optical system and incident from an oblique direction on the first reflection face and the second reflection face of the phase shifter is reflected as the first light beam and the second light beam by the respective reflection faces. At this time, since the first reflection face and the second reflection face have the above-described relationship, the second reflection face is inclined with respect to the first reflection face. Therefore, the optical axis of the first light beam and the optical axis of the second light beam are not parallel to each other but intersect with each other as they progress toward the light-receiving face of the detector, and at least a part of the incident regions of the both light beams overlaps on the light-receiving face.

How to incline the second reflection face with respect to the first reflection face will be described below.

Supposing that the axis orthogonal to the incident axis of the parallel light beam within the first reflection face is the x-axis, and the axis within the first reflection face orthogonal to the x-axis is the y-axis, let us consider a virtual plane which is generated by rotating the first reflection face by a predetermined angle about the x-axis and then rotating it by a predetermined angle about the y-axis. The second reflection face is set parallel to the virtual plane, and is set at a position neighboring the first reflection face. An optical path length difference is provided between the first light beam and the second light beam since the virtual plane is rotated from the first reflection face about the x-axis, and the first light beam and the second light beam enter the light-receiving face of the detector in a state where at least a part of the first light beam and the second light beam overlaps with the virtual plane rotated from the first reflection face about the y-axis. The angle at which the virtual plane is rotated about the x-axis and the angle at which the virtual plane is rotated about the y-axis are determined by the optical conditions of the combining optical system, the specifications (number of pixels, pixel pitch, and the like) of the detection element that detects the intensity distribution of the light on the light-receiving face of the detector, and the like.

In the above spectral measurement device, the phase shifter may include a transmissive optical element including a first transmission portion having a planar light-lead-in face and a planar light-lead-out face, and a second transmission portion having a planar light-lead-in face and a planar light-lead-out face, and may be configured so that the optical axis of the second light beam emitted from the light-lead-out face of the second transmission portion is inclined with respect to the optical axis of the first light beam emitted from the light-lead-out face of the first transmission portion.

In this configuration, the parallel light beam emitted from the combining optical system enters the light-lead-in face of the first transmission portion and the light-lead-in face of the second transmission portion, pass through the inside of each portion, and then are emitted from the light-lead-out face as the first light beam and the second light beam. At this time, assuming that the parallel light beams enters perpendicularly to, for example, the light-lead-in faces of the first and second transmission portions, the first light beam and the second light beam are refracted by an angle determined in accordance with an inclination angle of the light-lead-out face with respect to the light-lead-in face of each transmission portion and a refractive index difference between the transmissive optical element and the outside (atmosphere), and emitted from the light-lead-out face. Accordingly, by appropriately setting the inclination angles of the light-lead-out faces with respect to the light-lead-in faces of the first transmission portion and the second transmission portion, it is possible to cause the both light beams to enter the light-receiving face of the detector in a state where at least a part of the incident region overlaps with each other, while providing an optical path length difference between the first light beam and the second light beam.

In the spectral measurement device, it is possible to incline the optical axis of the second light beam with respect to the optical axis of the first light beam by configuring the phase shifter so that the light-lead-in faces of the first transmission portion and the second transmission portion are located on the same plane, and by configuring the phase shifter so that the light-lead-out face of the first transmission portion and the light-lead-out face of the second transmission portion are inclined at different angles with respect to the light-lead-in face. In this case, it is possible to design the phase shifter relatively easily if the first transmission portion has a configuration in which the light-lead-in face and the light-lead-out face are parallel to each other, and if the second transmission portion has a configuration in which the light-lead-out face is inclined with respect to the light-lead-in face.

The first transmission portion and the second transmission portion can be made of different transmission type optical members having different refractive indices, and the optical axis of the second light beam can be inclined with respect to the optical axis of the first light beam by utilizing the difference between the refractive index difference between the first transmission portion and the atmosphere and the refractive index difference between the second transmission portion and the atmosphere.

In the above spectral measurement device, since the phase shifter includes a transmissive optical element, in a case where the combining optical system includes an objective lens, it can include one transmissive optical element in which the combining optical system and the phase shifter are integrated, and it is hence possible to reduce the size of the spectral measurement device.

It is preferable in the above spectral measurement device, the combining optical system includes a plate-shaped first transmissive optical element having a convex light incident face and a planar light emission face positioned on the back side of the light incident face, the phase shifter includes a plate-shaped second transmissive optical element having a planar light incident face and a light emission face which is a face located on the back side of the light incident face and which includes two inclined faces having different inclinations from each other, and the spectral measurement device further includes a holding member configured to integrally hold the first transmissive optical element and the second transmissive optical element so that their optical axes coincide with each other.

In the above configuration, the first transmissive optical element and the second transmissive optical element are held by the holding member so that the light emission face of the first transmissive optical element and the light incident face of the second transmissive optical element are opposed to each other so as to be parallel to each other, and the optical axes of the first transmissive optical element and the second transmissive optical element coincide with each other. Thus, the combining optical system and the phase shifter are integrated. The light entering from the light incident face of the first transmissive optical element becomes a parallel light beam and is emitted from the light emission face, and enters the light incident face of the second transmissive optical element. Then, the parallel light beam incident on the second transmissive optical element is emitted from the two inclined faces constituting the light emission face as the first light beam and the second light beam, respectively.

It is preferable that the above spectral measurement device includes one transmissive optical element having a convex light incident face and a light emission face which is a face located on the back side of the convex light incident face and includes two inclined faces having different inclinations from each other, wherein the part of the transmissive optical element from the light incident face to the light emission face functions as the combining optical system, and the two inclined faces constituting the light emission face function as the phase shifter.

The above one transmissive optical element has such a shape in which the light emission face of the first transmissive optical element described above and the light incident face of the second transmissive optical element are joined. With this configuration, even when some external force acts on the spectral measurement device, the optical axes of the combining optical system and the phase shifter do not deviate, and it is thus possible to stably measure the spectral characteristics of the measurement point of the object to be measured.

It is preferable that in the above-mentioned spectral measurement device, the combining optical system is a Cassegrain optical system including a convex mirror and a concave mirror, the phase shifter is compose of a plate-shaped transmissive optical element having a planar light incident face and a light emission face which is a face located on the back side of the light incident face and which includes two inclined faces having different inclinations from each other, and the spectral measurement device further includes a holding member configured to integrally hold the Cassegrain optical system and the transmissive optical element so that their optical axes coincide with each other.

In the spectral measurement device according to the present invention, as the light emitted from a measurement point of an object to be measured, such light as, for example: scattered light or fluorescent light generated from the measurement point when light emitted from a light source is cast to the object to be measured; light which has been cast from the light source to the object to be measured and transmitted through the object to be measured; light reflected by the surface of the object to be measured; and the like, can be used.

The light source may be incorporated in the spectral measurement device, or it is possible to use a general-purpose light source device separate from the spectral measurement device. Sunlight can also be used as "light emitted by a light source".

The spectral measurement device according to the present invention may be configured so that the detector is a two-dimensional area sensor, and the processing unit sums up the intensity distribution of light by adding the intensity distribution of light detected on a line of the two-dimensional area sensor to the intensity distribution of light detected on another line by aligning the optical path length difference, and obtains the interferogram based on the summed up intensity distribution of light.

According to the above configuration, it is possible to lengthen the line for acquiring the interferogram (i.e., it is possible to increase the number of pixels corresponding to the line), and it is possible to enhance the wavelength resolution of the spectral characteristics.

Note that the processing of summing up the intensity distribution of light may be performed after the output signals of all pixels included in each of a certain line and another line of the two-dimensional area sensor are processed to obtain the intensity distribution of light of each line, or may be performed by processing the output signals of specific pixels of the pixels included in each line.

In a case where a region where the optical path length difference is the same (same optical path length difference region) exists in a certain line and another line, the output signals of the pixels included in the same optical path length difference region of any one of the lines may not be used for the calculation of the intensity distribution of light, or the output signals of the pixels included in the same optical path length difference regions of both lines may be totaled to use an averaged value for the calculation of the intensity distribution of light.

The present invention is also applicable to a method of measuring the spectral characteristics of a measurement point of an object to be measured. That is, a spectral measurement method according to the present invention includes:

a) combining light emitted from a measurement point of an object to be measured into one parallel light beam by means of a combining optical system;

b) dividing, by a phase shifter, a parallel light beam emitted from the combining optical system into a first light beam and a second light beam, emitting the first light beam and the second light beam toward a light-receiving face of a detector while providing an optical path length difference between the first light beam and the second light beam, and causing the first light beam and the second light beam to planarly enter the light-receiving face so that at least a part of an incident region of the first light beam on the light-receiving face and at least a part of an incident region of the second light beam overlap with each other; and c) obtaining an interferogram at the measurement point based on an intensity distribution of light in a region where an incident region of the first light beam and an incident region of the second light beam on the light-receiving face overlap, and acquiring a spectrum by Fourier-transforming the interferogram.

A transmissive optical element according to another aspect of the present invention is an optical element having a convex light incident face and a light emission face located on the back side of the convex light incident face and including two inclined faces having different inclinations from each other, wherein a light incident on the light incident face from a focal point of the light incident face is converted into a parallel light beam, and the parallel light beam is divided into a first light beam and a second light beam and an optical path length difference is provided between the first light beam and the second light beam, and the first light beam and the second light beam are emitted from the light emission face so that the first light beam and the second light beam overlap each other at least in a part on a face located at a predetermined distance from the light emission face.

Advantageous Effects of Invention

In the present invention, after combining the light emitted from the measurement point into one parallel light beam, the parallel light beam is divided into a first light beam and a second light beam, and an interference phenomenon between the first light beam and the second light beam is used to obtain an interferogram of the measurement point. In the present invention, by using a phase shifter having a characteristic configuration, an optical path length difference is provided between the first light beam and the second light beam, and the first light beam and the second light beam are caused to planarly enter the light-receiving face of the detector and to interfere, and it is hence possible to obtain an interference image having a wide area. Accordingly, it is possible to measure accurate and high wavelength-resolution spectral characteristics without increasing the size of the device. Since an optical member such as an imaging lens used for obtaining an interference image in a conventional spectral measurement device is not required, the size of the device can be small.

DESCRIPTION OF EMBODIMENTS

Hereinafter, a spectral measurement device according to the present invention will be specifically described.

First Embodiment

Figure 1A:
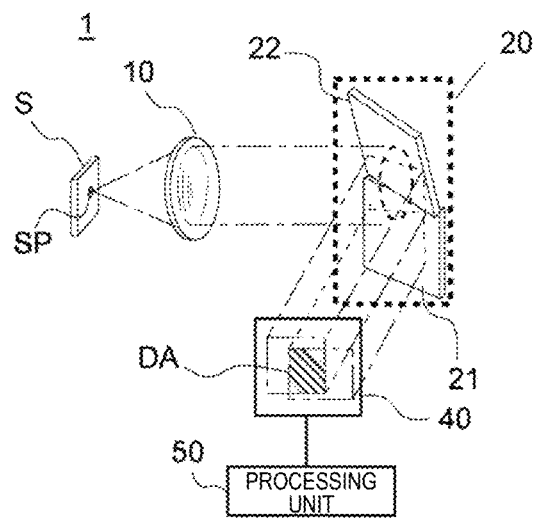
FIG. 1A is a schematic configuration view of a first embodiment of a spectral measurement device according to the present invention.

FIG. 1A is a schematic configuration view showing the first embodiment of a spectral measurement device according to the present invention. As shown in the figure, a spectral measurement device 1 includes an objective lens (collimator lens) 10, a phase shifter 20 having a reference mirror 21 and an inclined mirror 22, a detector 40 having a light-receiving face, and a processing unit 50 which processes a detection signal of the detector 40. The reference mirror 21 and the inclined mirror 22 each have a planar reflection face. The reflection face of the inclined mirror 22 and the reflection face of the reference mirror 21 are not parallel, and the other reflection face is inclined with respect to one reflection face. The detector 40 includes a two-dimensional area sensor such as a CCD camera in which a plurality of pixels is two-dimensionally arranged.

In the spectral measurement device 1 having the above configuration, when light is cast from a light source not shown to a measurement point SP on a sample S (object to be measured), and a light ray group (object light) such as scattered light and fluorescent light are generated from the measurement point SP, and when the object light passes through the objective lens 10, the object light is combined into one parallel light beam (hereinafter referred to as an "object beam"), and is introduced into each reflection face of the reference mirror 21 and the inclined mirror 22 of the phase shifter 20 from oblique directions. Accordingly, in this embodiment, the objective lens 10 functions as a combining optical system. The reflection face of the inclined mirror 22 is inclined with respect to the reflection face of the reference mirror 21, and the both reflection faces are not on the same plane. Therefore, the object beams incident on the respective reflection faces of the reference mirror 21 and the inclined mirror 22 are reflected toward different directions. Hereinafter, the object beams reflected by the respective reflection faces of the reference mirror 21 and the inclined mirror 22 are referred to as reference reflected light and inclined reflected light, respectively.

In the spectral measurement device 1, the respective reflection faces of the reference mirror 21 and the inclined mirror 22 are designed such that both of the reference reflected light and the inclined reflected light emitted from the respective reflection faces of the reference mirror 21 and the inclined mirror 22 planarly enter the light-receiving face of the detector 40, and the incident regions of both of the reference reflected light and the inclined reflected light overlap. Before the relationship between the reflection face of the reference mirror 21 and the reflection face of the inclined mirror 22 is described, the configuration of a conventional spectral measurement device will be described with reference to FIGS. 2A and 2B.

Figure 2A:
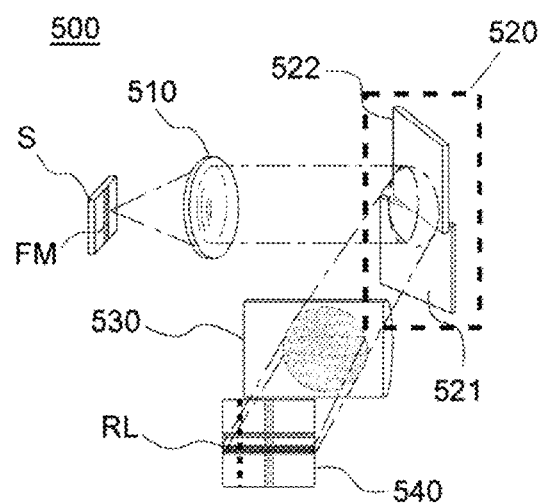
FIG. 2A is a schematic configuration view of a conventional spectral measurement device.

FIG. 2A is a schematic configuration view of a conventional device of the spectral measurement device 1. A spectral measurement device 500 corresponds to the spectral measurement device described in Patent Literature 2. As shown in the figure, the spectral measurement device 500 includes an objective lens (collimator lens) 510, a phase shifter 520 having a reference mirror 521 and an inclined mirror 522, an imaging lens (cylindrical lens) 530, a detector 540 having a light-receiving face at a position to be an imaging plane of the imaging lens 530, and a processing unit (not shown) which processes a detection signal of the detector 540. The reference mirror 521 and the inclined mirror 522 each have a planar reflection face.

In the spectral measurement device 500, when light is cast from a light source not shown to a linear measurement region FM on a sample S (object to be measured), and a light ray group (object light) such as scattered light and fluorescent light are generated from each bright point in the measurement region FM, and when the object light passes through the objective lens 510, the object light is combined into one parallel light beam (object beam), and is introduced into each reflection face of the reference mirror 521 and the inclined mirror 522 of the phase shifter 520 from oblique directions. Then, the object beams introduced into the respective reflection faces of the reference mirror 521 and the inclined mirror 522 are reflected at the same angle (reflection angle) as the incident angle, and then is directed to the imaging lens 530. Here, the object beams reflected by the respective reflection faces of the reference mirror 521 and the inclined mirror 522 are also referred to as reference reflected light and inclined reflected light, respectively.

Figure 2B:
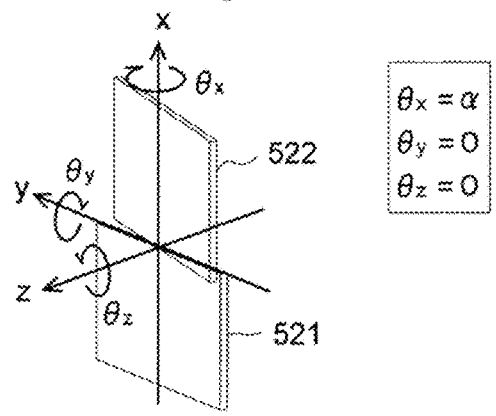
FIG. 2B is a view showing a relationship between a reference mirror and an inclined mirror of a phase shifter in the conventional spectral measurement device.

Now, the x-axis and y-axis, which are orthogonal coordinate axes defining the reflection face of the reference mirror 521, are defined as shown in FIG. 2B, and the axis orthogonal to the x-axis and the y-axis is defined as a z-axis. Then, the objective lens 510 and the reference mirror 521 of the phase shifter 520 are arranged so that the optical axis (incident axis) of the object beam entering the reflection face of the reference mirror 521 and a yz plane become parallel. With this arrangement, the x-axis is orthogonal to the incident axis of the object beam. Considering a virtual plane in which the reflection face of the reference mirror 521 is rotated by a predetermined angle θx about the x-axis with respect to the x-axis defined as described above, the inclined mirror 522 is installed so that the virtual plane and the reflection face of the inclined mirror 522 become parallel. As a result, the reflection face of the inclined mirror 522 is inclined in the y-axis direction with respect to the reflection face of the reference mirror 521, and the optical incident angle of the object beam with respect to each reflection face is different, and hence the angle formed by the z-axis and the optical axis of the reference reflected light is different from the angle formed by the z-axis and the optical axis of the inclined reflected light.

Specifically, for example, when the incident angle of the object beam with respect to the reflection face of the reference mirror 521 is 45° and the rotation angle θx of the reflection face of the inclined mirror 522 about the x-axis is α°, the angle formed by the reflection face of the inclined mirror 522 and the incident axis of the object beam is (45+α)°, and the incident angle of the object beam with respect to the reflection face of the inclined mirror 522 is (45−α)°. Therefore, while the angle (This corresponds to the reflection angle.) formed by the z-axis and the optical axis of the reference reflected light is 45°, the angle formed by the z-axis and the optical axis of the inclined reflected light is (45−2α)°, and the traveling direction of the inclined reflected light deviates by 2α° in the y-axis direction with respect to the traveling direction of the reference reflected light. This deviation angle causes a continuous optical path length difference between the reference reflected light and the inclined reflected light.

However, the reflection face of the inclined mirror 522 is only inclined in the y-axis direction with respect to the reflection face of the reference mirror 521, and the reference reflected light and the inclined reflected light do not intersect. Therefore, in the conventional spectral measurement device 500, the imaging lens 530 is arranged between the phase shifter 520 and the detector 540. By passing through the imaging lens 530, the reference reflected light and the inclined reflected light focus on a straight line RL orthogonal to the measurement region FM, which is on the light-receiving face of the detector 540 to form a linear interference image. Accordingly, it is obtained an interferogram of each bright point by measuring the change in light intensity along the linear interference image, and it is obtained the spectral characteristics of each bright point by Fourier-transforming the interferogram.

Figure 1B:
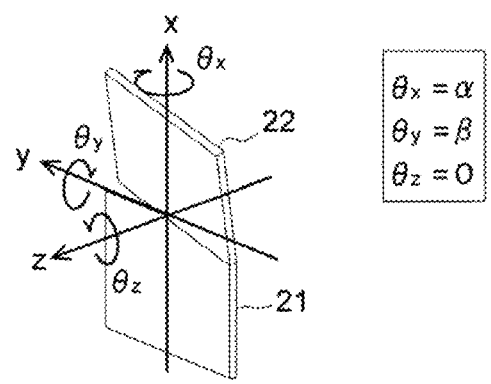
FIG. 1B is a view showing a relationship between a reference mirror and an inclined mirror of a phase shifter in the spectral measurement device.

On the other hand, FIG. 1B shows the relationship between the reference mirror 21 and the inclined mirror 22 of the phase shifter 20 in the spectral measurement device 1 according to the present embodiment. The definitions of the x-axis, the y-axis, and the z-axis, and the arrangement of the objective lens 10 and the reference mirror 21 are the same as those in the spectral measurement device 500.

In the spectral measurement device 1, considering a virtual plane in which the reflection face of the reference mirror 21 is rotated by the predetermined angle θx about the x-axis and rotated by a predetermined angle θy about the y-axis, the inclined mirror 22 is installed so that the virtual plane and the reflection face of the inclined mirror 22 become parallel. As a result, the reflection face of the inclined mirror 22 is inclined in the y-axis direction and the z-axis direction with respect to the reflection face of the reference mirror 21.

When θx=α° and θy=β°, the traveling direction of the inclined reflected light deviates with respect to the traveling direction of the reference reflected light by 2α° in the y-axis direction by the inclination (rotation about the x-axis) in the y-axis direction, and this deviation angle causes an optical path length difference between the reference reflected light and the inclined reflected light. By the inclination in the z-axis direction (rotation about the y-axis), the traveling direction of the inclined reflected light is inclined in the z-axis direction, and the inclined reflected light and the reference reflected light intersect at a predetermined distance from the phase shifter 20. The distance from the phase shifter 20 to the point where both reflected lights intersect is determined according to the angle θy=β°, and the light-receiving face of the detector 40 is arranged at such a point.

Due to this, in the spectral measurement device 1, as shown in FIG. 1A, the reference reflected light and the inclined reflected light emitted from the respective reflection faces of the reference mirror 21 and the inclined mirror 22 planarly enter a light-receiving face 41 of the detector 40, and a part of each incident region overlaps. As described above, since there is an optical path length difference between the reference reflected light and the inclined reflected light, an interference image of the reference reflected light and the inclined reflected light is formed in a region where the incident region of the reference reflected light and the incident region of the inclined reflected light overlap (overlap region DA). Accordingly, it is obtained an interferogram of the measurement point SP by detecting the intensity distribution of light of this interference image, and it is obtained the spectral characteristics of the measurement point SP by Fourier-transforming the interferogram.

Next, the interference image formed on the light-receiving face of the detector 40 will be described in detail with reference to FIGS. 3A to 3D.

By passes through the objective lens 10, the object light generated from the measurement point SP is combined into one object beam BL, and then enters the respective reflection faces of the reference mirror 21 and the inclined mirror 22 of the phase shifter 20, and is emitted as reference reflected light La and inclined reflected light Lb, respectively. It is assumed that the same amount of object beam BL enters respectively the reference mirror 21 and the inclined mirror 22. Then, the reference reflected light La and the inclined reflected light Lb are directed toward the detector 40, and enter the light-receiving face 41 in a state where the incident region of the reference reflected light La and the incident region of the inclined reflected light Lb overlap, and an interference image is formed in the overlap region DA (See FIG. 3A).

Figure 3A:
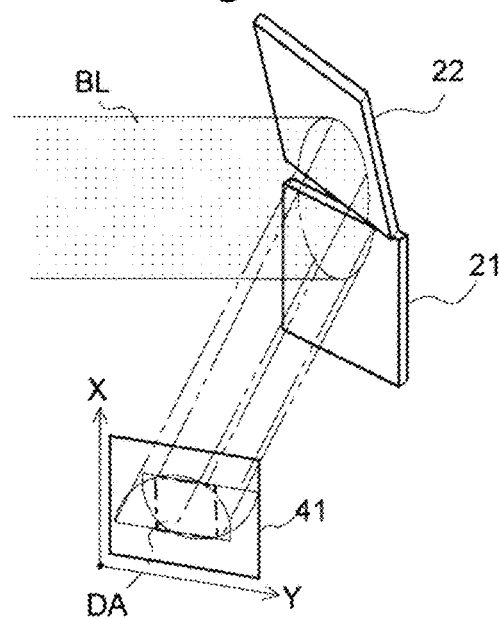
FIG. 3A is a view of formation of an interference image of the reference reflected light and the inclined reflected light on a light-receiving face of a detector as viewed from the back side of the light-receiving face.
Figure 3B:
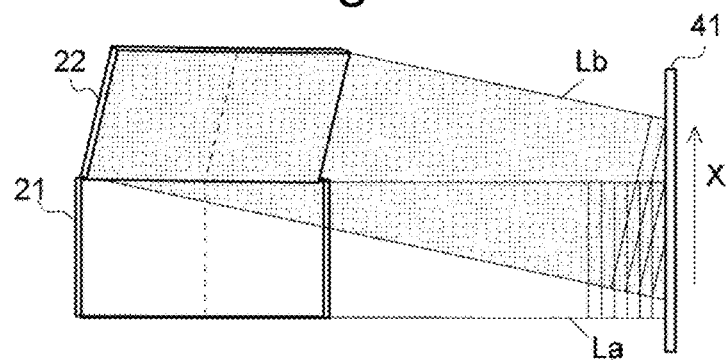
FIG. 3B is a view of formation of an interference image of the reference reflected light and the inclined reflected light on a light-receiving face of a detector as viewed from the side of the light-receiving face.
Figure 3C:
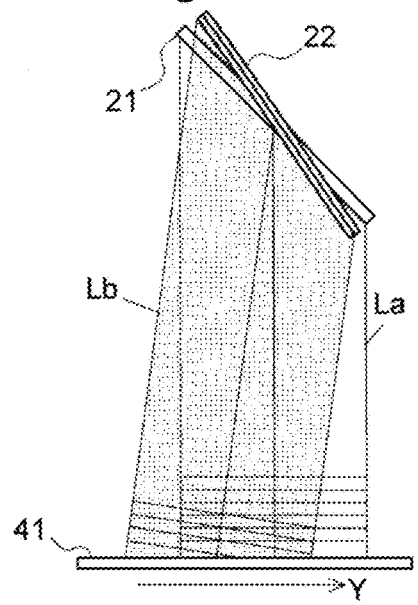
FIG. 3C is a view of formation of an interference image of the reference reflected light and the inclined reflected light on a light-receiving face of a detector as viewed from above the light-receiving face.
Figure 3D:
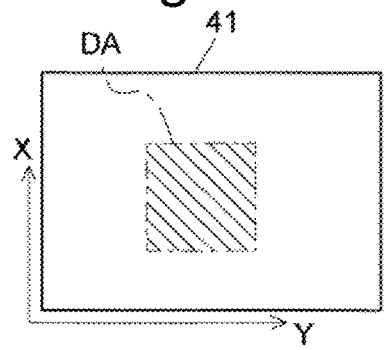
FIG. 3D is a view showing an interference image of the reference reflected light and the inclined reflected light formed on the light-receiving face of the detector.

When the axis in the light-receiving face 41 of the detector 40 extending in the direction (up and down direction) in which the reference mirror 21 and the inclined mirror 22 are aligned is defined as an X-axis, and the axis orthogonal to the X-axis is defined as a Y-axis, as shown in FIGS. 3B and 3C, the wave front of the inclined reflected light Lb inclines in both directions of the X-axis direction and the Y-axis direction with respect to the wave front of the reference reflected light La, and hence the optical path length difference between the both reflected lights changes along the X-axis direction and the Y-axis direction in the overlap region DA. Therefore, when points where the optical path length difference becomes the same in the overlap region DA are connected by a line, the line is inclined with respect to the X-axis and the Y-axis as shown in FIG. 3D.

Figure 4:
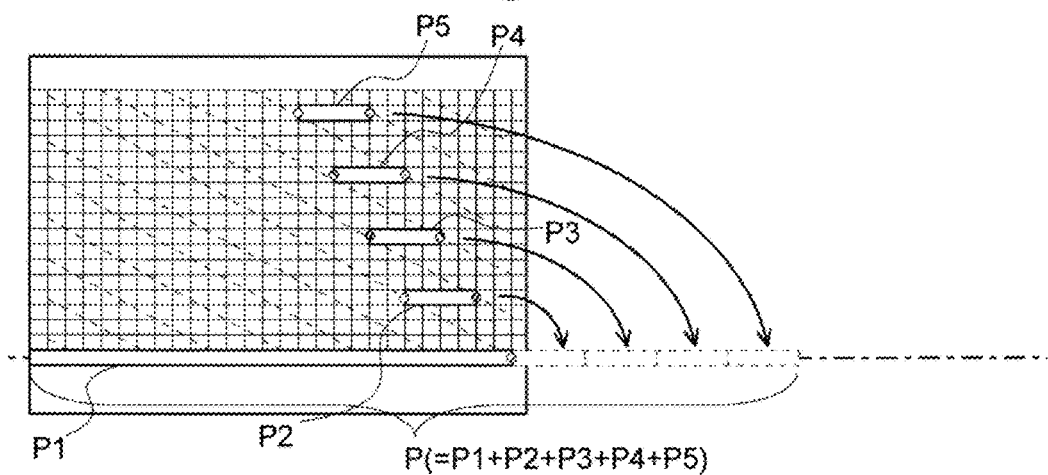
FIG. 4 is an explanatory view of an analysis line for obtaining an interferogram.

Therefore, the processing unit 50 of the spectral measurement device 1 performs processing of summing up the intensity distribution of the light detected on a certain line of the two-dimensional area sensor serving as the detector 40 and the intensity distribution of the light detected on another line by aligning the optical path length difference. Specifically, for example, as shown in FIG. 4, in a case where the optical path length difference of the right end portion of the interference image detected in a pixel row P1 on the lowest line and the optical path length difference of the left end portion of the interference image detected in a pixel row P2 located on the line four steps higher than the pixel row P1 are the same, the pixel row P2 is virtually connected to the right side of the pixel row P1. Similarly, a pixel row P3 located four steps higher than the pixel row P2 is virtually connected to the right side of the pixel row P2, a pixel row P4 located four steps higher than the pixel row P3 is virtually connected to the right side of the pixel row P3, and a pixel row P5 located four steps higher than the pixel row P4 is virtually connected to the right side of the pixel row P4, thereby obtaining an analysis line P (=P1+P2+P3+P4+P5). Then, the interferogram is obtained from the output values of the pixels included in the analysis line P, and this interferogram is Fourier-transformed to obtain the spectral characteristics (spectrum).

According to such a method, since the number of pixels for obtaining the interferogram is increased as compared with the case where he interferogram is obtained from the output value of the pixel row P1, it is possible to acquire the spectral characteristics in a wide wavelength range and high wavelength resolution.

Hereinafter, an experiment result of measuring the spectral characteristics using the spectral measurement device 1 will be described.

Experiment 1

Figure 5:
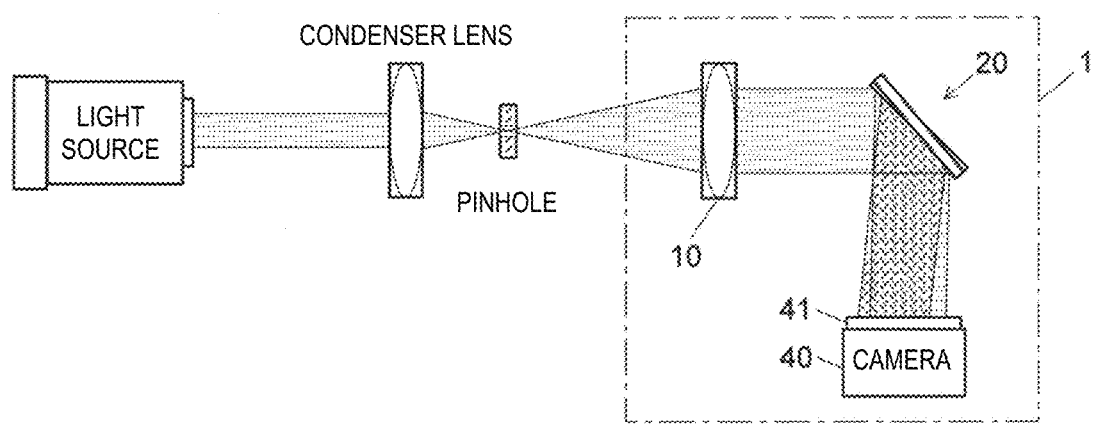
FIG. 5 is a schematic configuration view of a spectral characteristic device used in Experiment 1.

In this experiment, as shown in FIG. 5, light emitted from a light source emitting directional light was passed through a condenser lens and a pinhole in this order, and then caused to enter the objective lens 10 of the spectral measurement device 1. The light incident on the objective lens 10 was combined into one parallel light beam by the objective lens 10, and then introduced into the phase shifter 20, and the reflected light (reference reflected light and inclined reflected light) enters a camera serving as the detector 40. The specifications of the light source, the condenser lens, the pinhole, the objective lens 10, and the camera (detector 40) used in the experiment are as follows.

Light source: $CO_2$ laser (Model: RF4, Access Laser Company) which outputs a laser light having a central wavelength of 10.6 μm
Condenser lens: Focal length f=100 mm
Pinhole: 50 μm in diameter
Objective lens: Focal length f=200 mm
Camera: Infrared camera module C200V with 320×240 pixels (Nippon Avionics Co., Ltd.)

Figure 6:
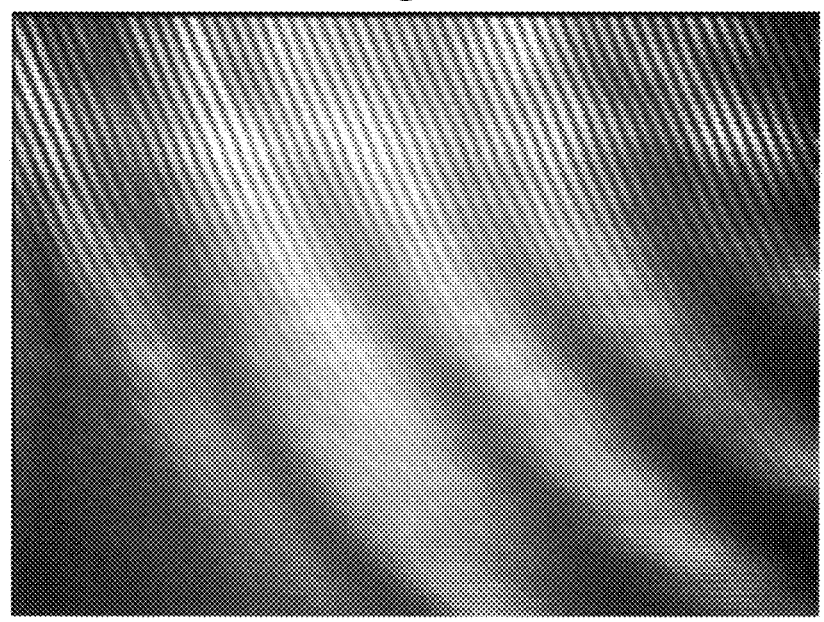
FIG. 6 is an observation image by a camera.
Figure 7A:
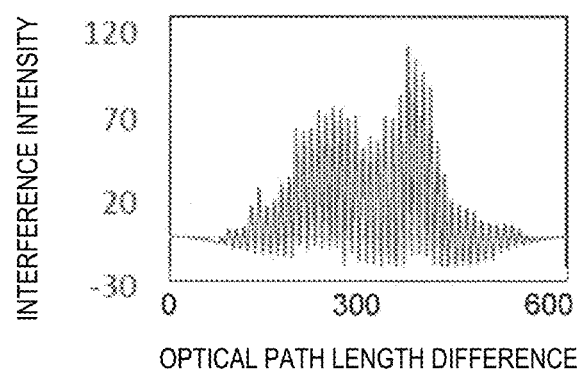
FIG. 7A is an interferogram of $CO_2$ laser light emitted from a light source.
Figure 7B:
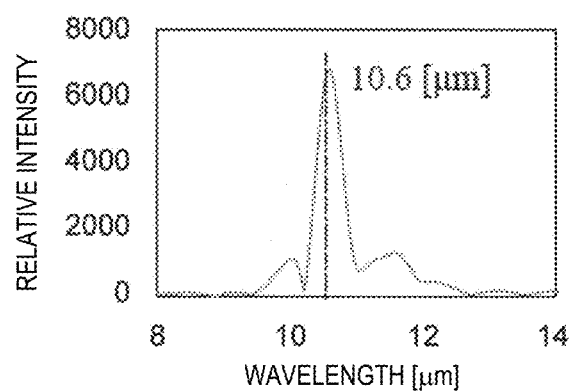
FIG. 7B is spectral characteristics of $CO_2$ laser light emitted from the light source.

FIG. 6 is an image captured by the camera. As can be seen from the figure, clear interference fringes were observed in this experiment. Next, the intensity distribution of light was obtained from the output value of the camera, the interferogram was obtained based on this intensity distribution, and the interferogram was Fourier-transformed to obtain the spectral characteristics. The results are shown in FIGS. 7A and 7B. FIG. 7A is an interferogram, and FIG. 7B is spectral characteristics (spectrum). Here, the intensity distribution of light was obtained from the output values of pixels on a certain line, among the pixels (320×240 pixels) included in the camera.

As shown in FIG. 7B, in this experiment, a spectrum having a clear peak at 10.6 μm, which is the central wavelength of the laser light output from the $CO_2$ laser, was obtained. This indicates that it is possible to acquire the spectral characteristics of the laser light with high accuracy by the spectral measurement device 1 used in this experiment.

Experiment 2

Figure 8:
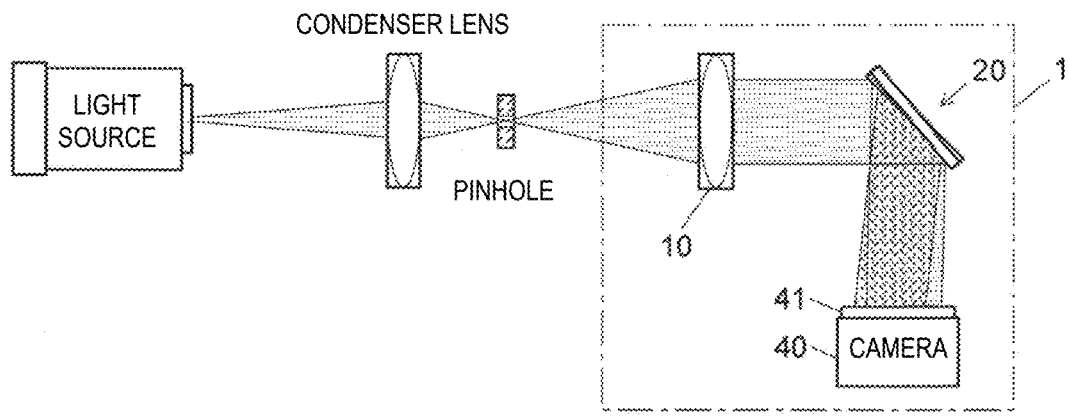
FIG. 8 is a schematic configuration view of a spectral characteristic device used in Experiment 2.

In this experiment, as shown in FIG. 8, light emitted from a light source emitting non-directional light was passed through a condenser lens and a pinhole in this order, and then caused to enter the objective lens 10 of the spectral measurement device 1. The specifications of the light source, the condenser lens, the pinhole, the objective lens, and the camera used in the experiment are as follows.

Light source: Filament type mid-infrared white light source (Kanthal Filament IR Source, Model: EK8620, HELIOWORKS)
Condenser lens: Focal length f=100 mm
Pinhole: 1 mm in diameter
Objective lens: Focal length f=25 mm
Camera: Infrared camera module C200V with 320×240 pixels (Nippon Avionics Co., Ltd.)

Figure 9:
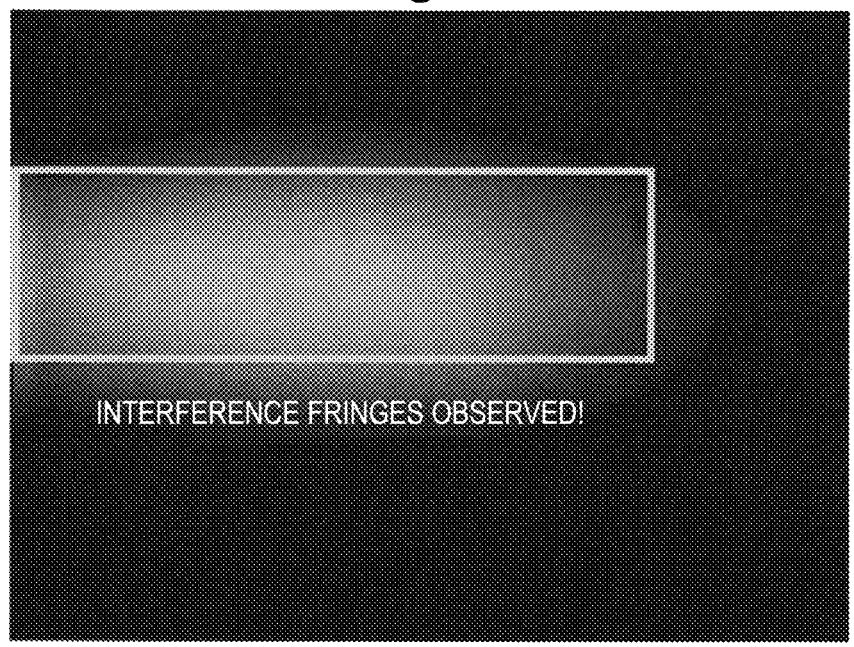
FIG. 9 is an observation image by the camera.
Figure 10A:
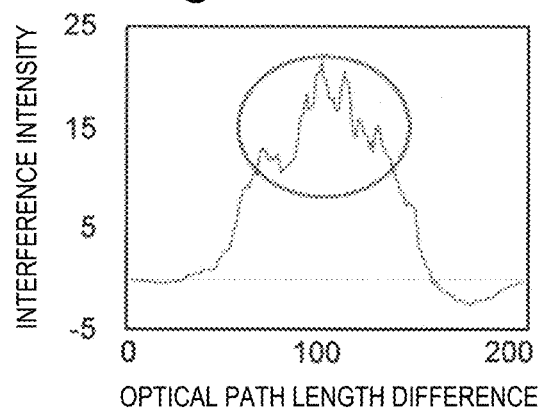
FIG. 10A is an interferogram of mid-infrared white light emitted from the light source.
Figure 10B:
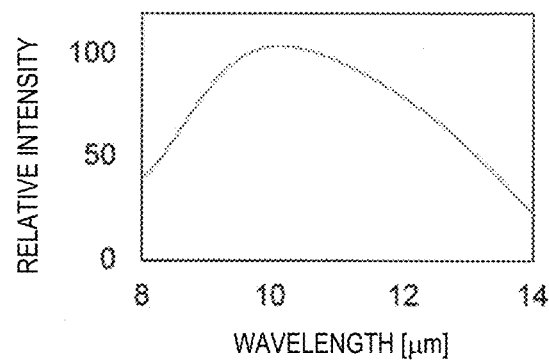
FIG. 10B is spectral characteristics of mid-infrared white light emitted from the light source.

FIG. 9 is an image captured by the camera. As can be seen from the figure, interference fringes were observed in this experiment, although not as clear as the captured image obtained in Experiment 1 above. Next, the intensity distribution of light was obtained from the output value of the camera, the interferogram was obtained based on this intensity distribution, and the interferogram was Fourier-transformed to obtain the spectral characteristics. The results are shown in FIGS. 10A and 10B. FIG. 10A is an interferogram, and FIG. 10B is spectral characteristics (spectrum). Here, the intensity distribution of light was obtained from the output values of pixels on a certain line, among the pixels (320×240 pixels) included in the camera.

As can be seen from a comparison between FIGS. 10A and 10B and FIGS. 7A and 7B, in this experiment, spectral characteristics according to the interferogram and Planck's law were successfully acquired. This demonstrated the possibility of spectral measurement in the mid-infrared region.

Experiment 3

Next, an experiment was conducted to verify that the wavelength resolution of the spectral characteristics was improved by the processing of summing up (summing processing) the output values of pixels on a plurality of lines. The specifications of the objective lens 10 and the detector 40 (camera) of the spectral measurement device 1 used in this experiment, and the specifications of the light source, the condenser lens, and the pinhole are the same as those in Experiment 1.

Figure 11:
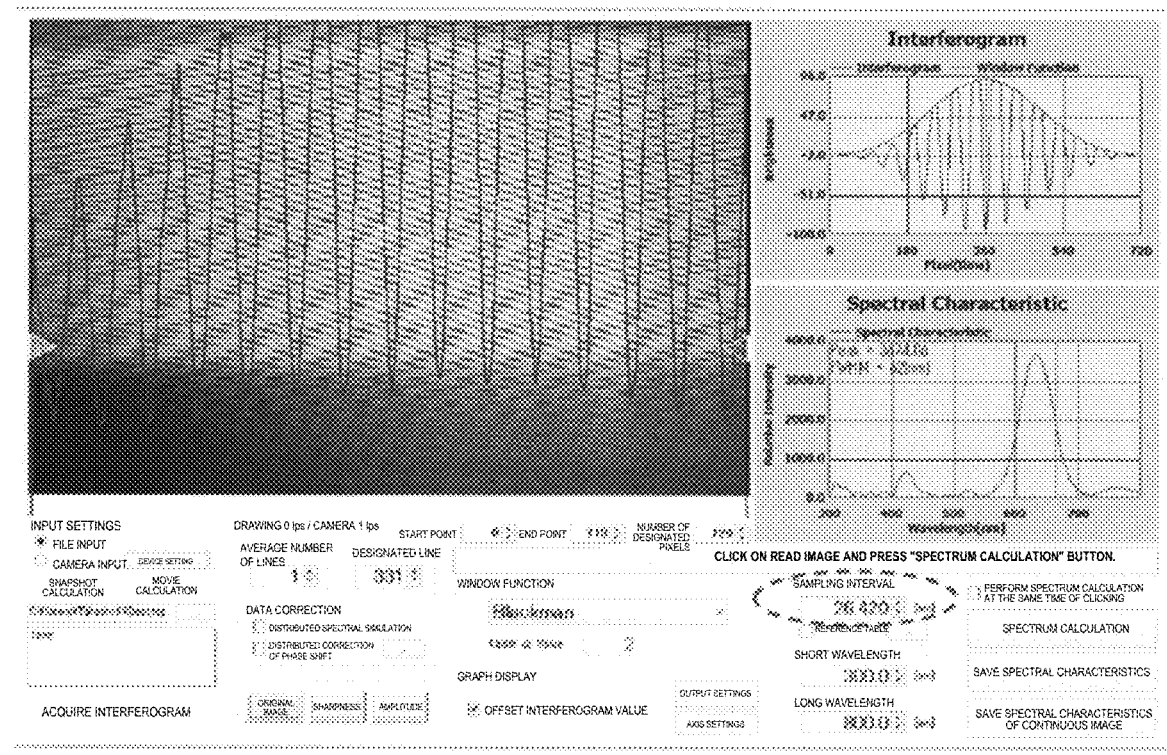
FIG. 11 shows a result of Experiment 3, and is an example of a display screen showing an intensity distribution of light detected in pixels on a certain line, an interferogram and a spectrum obtained from this intensity distribution of light.
Figure 12:
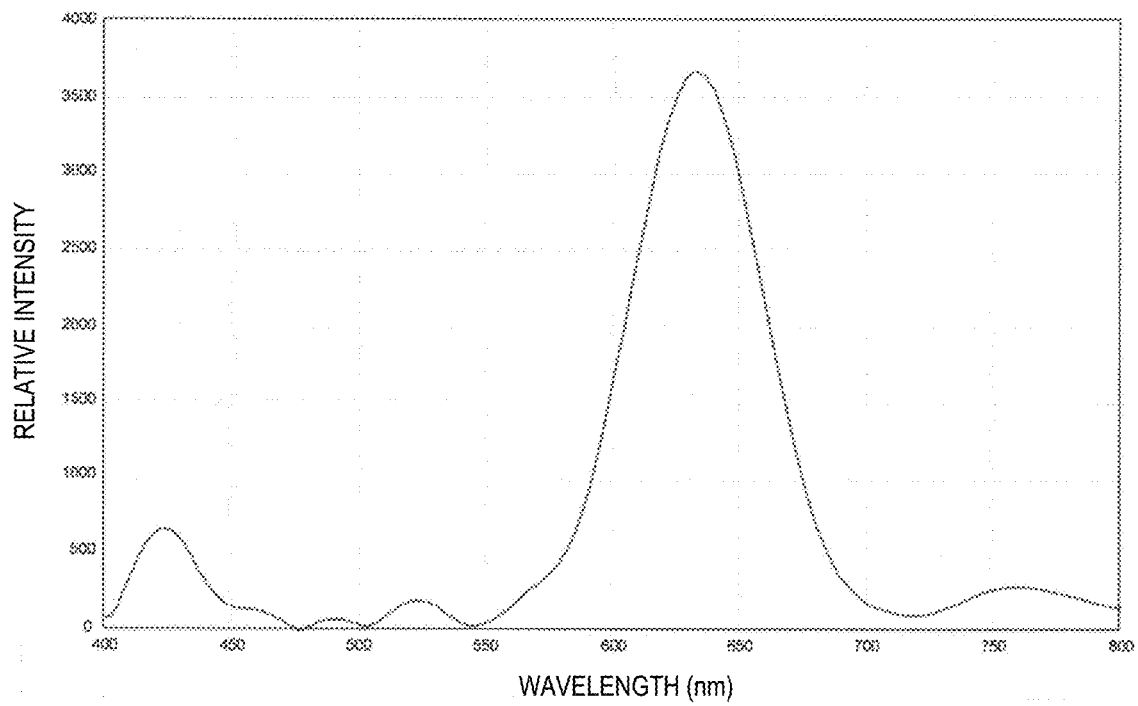
FIG. 12 is an enlarged view of the spectrum shown on the display screen of FIG. 11.

FIG. 11 shows a display screen showing the interferogram and the spectral characteristics before summing up the output values of pixels on the plurality of lines, i.e., obtained from the output values of pixels on one line, and FIG. 12 shows an enlarged view of the spectral characteristics shown in FIG. 11. The image displayed in the upper left region of FIG. 11 is an image captured by the camera.

Figure 13:
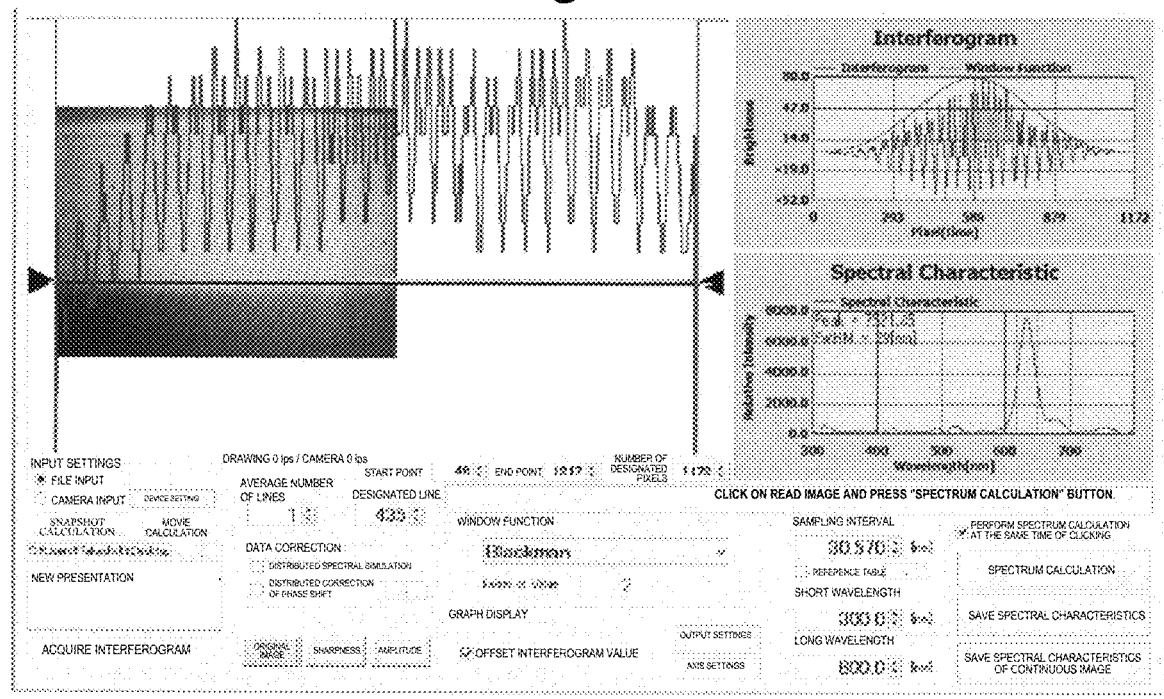
FIG. 13 is an example of a display screen showing an intensity distribution of light obtained by summing up an intensity distribution of light detected in pixels on a certain line and an intensity distribution of light detected in pixels on another line, an interferogram and a spectrum obtained from the summed up intensity distribution of light.
Figure 14:
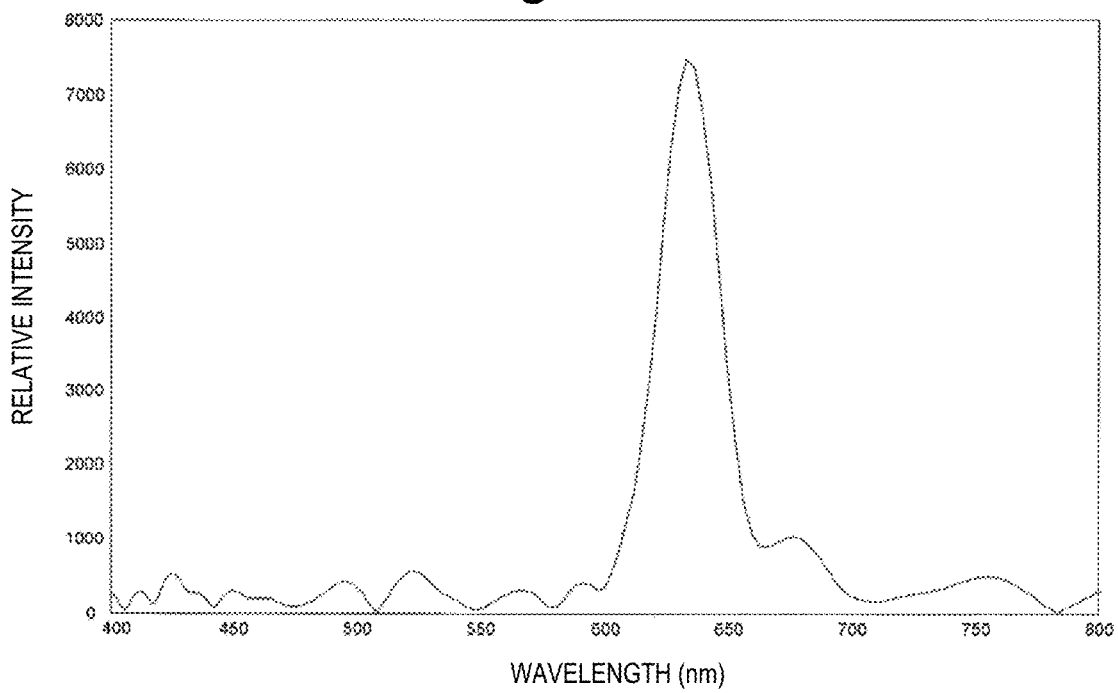
FIG. 14 is an enlarged view of the spectrum shown on the display screen of FIG. 13.

On the other hand, FIG. 13 shows a display screen showing the interferogram and the spectral characteristics obtained from the intensity distribution of light obtained by summing up the output values of pixels on one line and the output values of pixels on another line. FIG. 14 shows an enlarged view of the spectral characteristic shown in FIG. 13. The image shown in the upper left region of FIG. 13 is a reduced image of the captured image displayed in the upper left region of FIG. 11.

As can be seen from the comparison between FIG. 12 and FIG. 14, although peaks appeared in the same wavelength range in both spectral characteristics, the half width of the peak, which was 62 nm before summed up, became 29 nm by the processing of summing up the output values of pixels on the plurality of lines. This has verified that high wavelength resolution is successfully realized by the summing processing.

Experiment 4

In this experiment, transmitted light when light having a wavelength of 1520 to 1620 nm was cast to a container containing a glucose aqueous solution adjusted to various concentrations was caused to enter the objective lens 10 of the spectral measurement device 1. The specifications of the objective lens 10 and the detector 40 (camera) of the spectral measurement device 1 used in this experiment, and the specifications of the light source, the condenser lens, and the pinhole are the same as those in Experiment 1.

Figure 15:
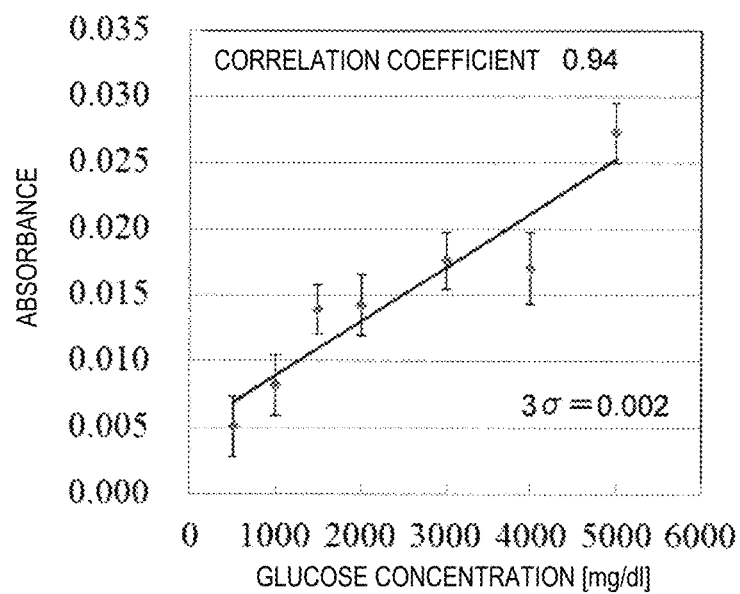
FIG. 15 is a correlation view between glucose concentration and absorbance, showing a result of Experiment 4.
Figure 16:
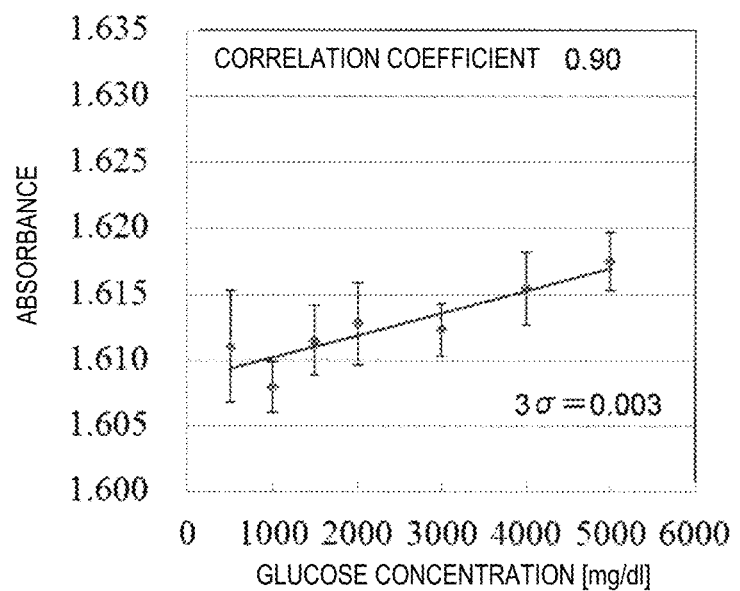
FIG. 16 is a correlation view between glucose concentration and absorbance, showing a result of a comparative experiment of Experiment 4.

The glucose concentrations used in this experiment were 500, 1000, 1500, 2000, 3000, 4000, and 5000 mg/dL, and the number of samples of the glucose solution at each concentration was 60 (n=60). The measurement results are shown in FIG. 15. For comparison, the absorbance of glucose solution at each concentration was measured using a conventional monochromator. The results are shown in FIG. 16.

The correlation coefficient of the results measured by the spectral measurement device 1 was 0.94, and the correlation coefficient of the results measured by the monochromator was 0.90. This result indicates that the spectral measurement device 1 can measure the glucose concentration with the same accuracy as that of a conventional general monochromator.

Second Embodiment

The above-described spectral measurement device 1 is an example in which the phase shifter 20 includes a mirror, but the phase shifter can include a transmission optical member instead.

Figure 17A:
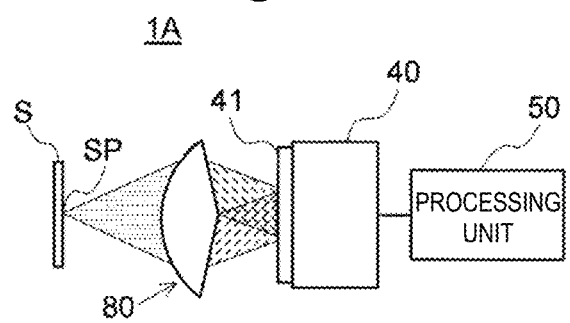
FIG. 17A is a schematic configuration view of a second embodiment of the spectral measurement device according to the present invention.

That is, FIG. 17A shows a second embodiment of the spectral measurement device according to the present invention. A spectral measurement device 1A of the second embodiment includes a transmissive optical element 80, the detector 40 having the light-receiving face 41, and the processing unit 50 which processes a detection signal of the detector 40. Similarly to the first embodiment, the detector 40 includes a two-dimensional area sensor such as a CCD camera in which a plurality of pixels is two-dimensionally arranged. The object light emitted from the measurement point SP of the sample S enters the transmissive optical element 80, and is combined into a parallel light beam (object beam), thereafter, is divided into a first light beam and a second light beam, and each planarly enters the light-receiving face 41 of the detector 40.

Figure 17B:
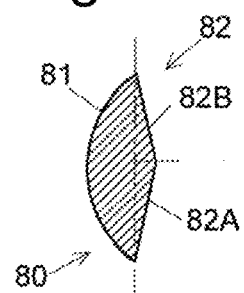
FIG. 17B is a longitudinal sectional view of a transmissive optical element.

As shown in FIG. 17B, the transmissive optical element 80 includes a convex face portion 81, which is a face on the sample side, and a phase shifter portion 82, which is a face on the opposite side, and the phase shifter portion 82 further includes a first transmission portion 82A and a second transmission portion 82B above it. The convex face portion 81 corresponds to the objective lens 10 in the first embodiment, and functions as a combining optical system which combines object light emitted from the measurement point SP into parallel light beams. On the other hand, the phase shifter portion 82 functions as the phase shifter of the present invention.

Figure 18A:
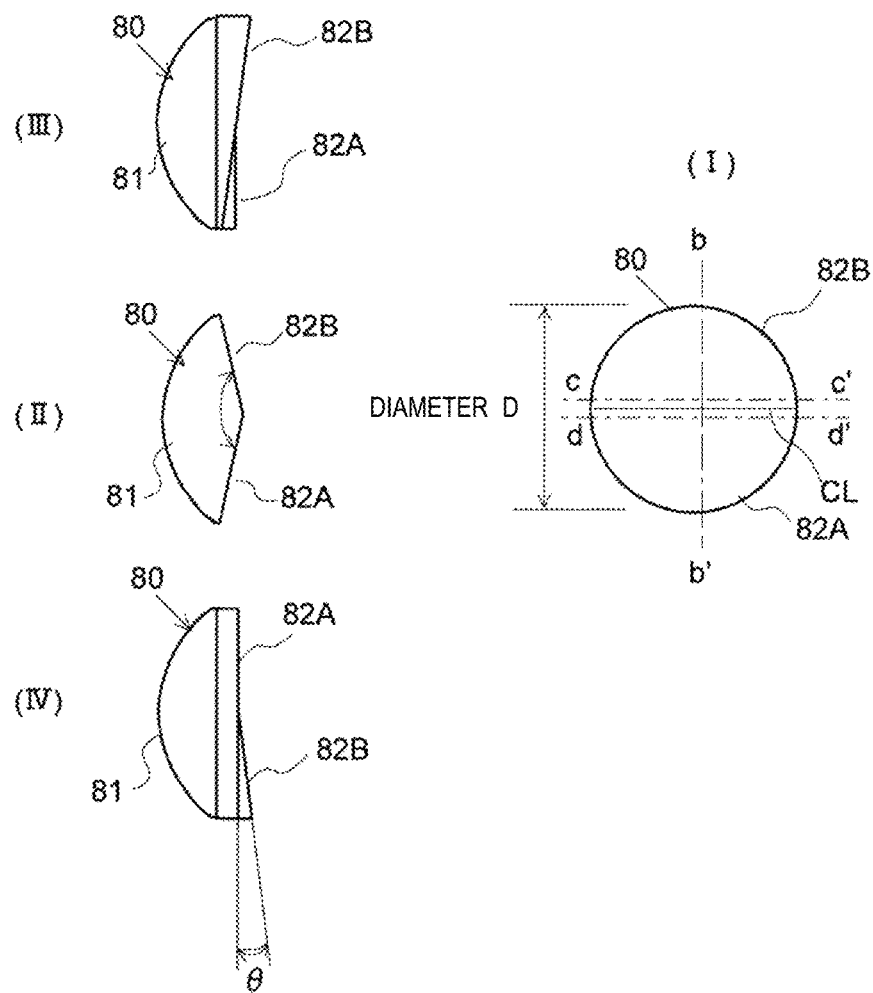
FIG. 18A is a view (I) of a transmissive optical element constituting a phase shifter in the spectral measurement device of the second embodiment as viewed from the detector side, a sectional view (II) along a line b-b' in Fig. (I), a sectional view (III) along a line c-c' in Fig. (I) as viewed from above, and a sectional view (IV) along a line d-d' in Fig. (I) as viewed from below.
Figure 18B:
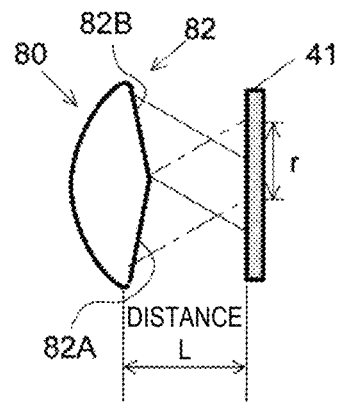
FIG. 18B is a view for explaining a scene in which light emitted from a transmissive optical element enters a light-receiving face of a detector.

FIG. 18A is a view (I) of the transmissive optical element 80 as viewed from the phase shifter portion 82 side, a sectional view (II) along the line b-b' in Fig. (I), a sectional view (III) along the line c-c' in Fig. (I) as viewed from above, and a sectional view (IV) along the line d-d' in Fig. (I) as viewed from below. FIG. 18B shows a scene in which light (first light beam and second light beam) emitted from the first transmission portion 82A and the second transmission portion 82B of the phase shifter portion 82 of the transmissive optical element 80 enter the light-receiving face 41 of the detector 40. In this paragraph and the next paragraph, the top, bottom, right, and left in Fig. (I) of FIG. 18A will be described as the top, bottom, right, and left of the phase shifter portion 82.

As is obvious from FIGS. 18A and 18B, the face of the first transmission portion 82A of the phase shifter portion 82 and the face of the second transmission portion 82B are inclined downward and upward from a vertical center line CL of the phase shifter portion 82, respectively, toward the convex face portion 81. Thus, the thicknesses of the first transmission portion 82A and the second transmission portion 82B are gradually reduced downward and upward from the center line CL. However, the inclination angle of the face of the first transmission portion 82A and the inclination angle of the face of the second transmission portion 82B are slightly different. On the other hand, while the thickness of the first transmission portion 82A is constant in the left-right direction, the thickness of the second transmission portion 82B is larger on the left side than on the right side. That is, the face of the second transmission portion 82B is inclined upward from the center line CL and inclined from the left side toward the right side.

According to the above configuration, by passing through the convex face portion 81, the object light incident on the convex face portion 81 of the transmissive optical element 80 becomes a parallel light beam (object beam), and further passes through the first transmission portion 82A and the second transmission portion 82B, and is refracted at an angle corresponding to an inclination angle of each face, a wavelength of the object beam, and a refractive index difference between the transmissive optical element 80 and the outside (air) when emitted from these faces. Accordingly, by appropriately selecting the material of the transmissive optical element 80, the inclination angles of the faces of the first transmission portion 82A and the second transmission portion 82B, a distance L from the transmissive optical element 80 to the light-receiving face 41 of the detector 40, and the like, it is possible to cause the first light beam and the second light beam emitted from the first transmission portion 82A and the second transmission portion 82B to enter the light-receiving face 41 in a state where at least a part of the incident region of each light beam overlaps on the light-receiving face 41.

The inclination angle of the face of the second transmission portion 82B with respect to the face of the first transmission portion 82A is designed based on optical conditions such as a measurement wavelength range and a wavelength resolution.

For example, when a diameter D of the transmissive optical element 80 is 6 mm, the distance L from the transmissive optical element 80 to the light-receiving face 41 of the detector 40 is 20 mm, the number of pixels of the detector 40 is 80×80, the vertical and horizontal pixel pitches are both 34 μm, and the measurement wavelength range is 8 to 14 µm, the first light beam and the second light beam enter the light-receiving face 41 in a state where at least a part of the incident region of each light beam overlaps on the light-receiving face 41 by setting the angle θ to 1.12 deg and an angle φ to 177.15 deg where the inclination angle (horizontal inclination angle) of the face of the second transmission portion 82B with respect to the face of the first transmission portion 82A is θ, and the angle formed by the faces of the first transmission portion 82A and the second transmission portion 82B (vertical inclination angle) is φ.

Third Embodiment

Figure 19:
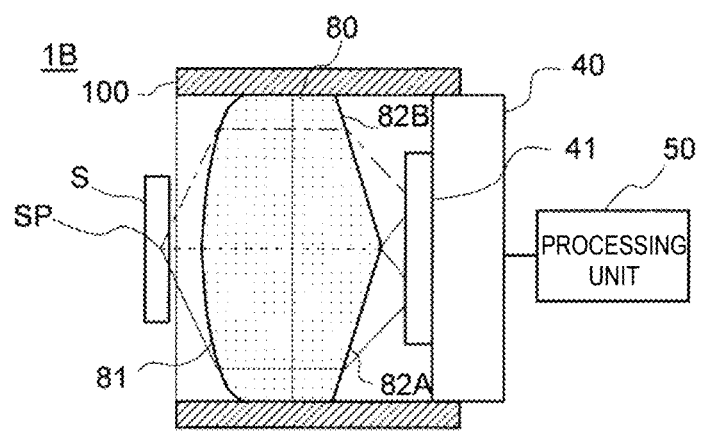
FIG. 19 is a schematic configuration view of the spectral measurement device of a third embodiment.

FIG. 19 is a schematic configuration view of the spectral measurement device of a third embodiment of the present invention. A spectral measurement device 1B of this embodiment is different from that in the second embodiment in that the transmissive optical element 80 and the detector 40 are contained in the one container 100. Since the other components of the spectral measurement device are substantially the same as those of the second embodiment, the same reference numerals are given to the same components, and the description will be omitted.

The container 100 contains the transmissive optical element 80 and the detector 40 so that the distance L from a light emission face 82 of the transmissive optical element 80 to the light-receiving face 41 of the detector 40 becomes a predetermined length. Here, the distance L is set to a length such that the first light beam and the second light beam emitted from the first transmission portion 82A and the second transmission portion 82B of the transmissive optical element 80 enter the light-receiving face 41 of the detector 40 in a state where at least a part of the first light beam and the second light beam overlap. According to this configuration, it is possible to provide the spectral measurement device 1B resistant to disturbance.

In the container 100, by configuring the transmissive optical element 80 to be movable relative to the detector 40, it is possible to adjust the distance L according to the measurement wavelength range or the like.

Furthermore, the distance from the end portion of the container 100 opposite to the detector 40 to the light incident face 81 of the transmissive optical element 80 is preferably set to a focal length of the light incident face 81 side of the transmissive optical element 80 or the focal length −α. In this configuration, by bringing the end portion of the container 100 into contact with the face of the sample S, the object light from the measurement point SP located on the face of the sample S or the measurement point SP located inward by the distance α from the face can be converted into a parallel light beam by the convex face portion 81 of the transmissive optical element 80.

Fourth Embodiment

Figure 20:
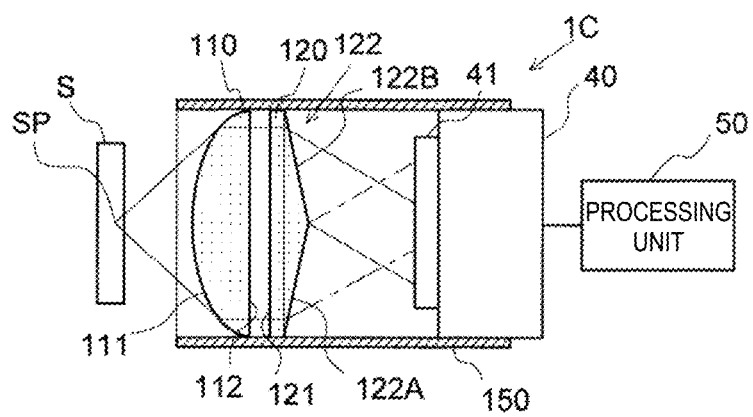
FIG. 20 is a schematic configuration view of a fourth embodiment of the spectral measurement device according to the present invention.

FIG. 20 is a schematic configuration view of the fourth embodiment of the spectral measurement device according to the present invention. In a spectral measurement device 1C of this embodiment, the interference optical system includes two transmissive optical elements (first transmissive optical element and second transmissive optical element). Hereinafter, the first transmissive optical element is referred to as a collimated optical element 110, and the second transmissive optical element is referred to as a division optical element 120.

The collimated optical element 110 has a convex light incident face 111 and a planar light emission face 112 on the back side of the convex light incident face 111. The division optical element 120 has a planar light incident face 121 and a convex light emission face 122 on the back side of the planar light incident face 121.

The light emission face 122 of the division optical element 120 includes a planar first light emission face 122A and a second light emission face 122B arranged side by side. The first light emission face 122A and the second light emission face 122B correspond to the face of the first transmission portion 82A and the face of the second transmission portion 82B, respectively, of the transmissive optical element 80 included in the spectral measurement device 1A of the second embodiment, and the respective inclination angles of the first light emission face 122A and the second light emission face 122B and the angles formed by the both are the same as those of the face of the first transmission portion 82A and the face of the second transmission portion 82B. Accordingly, a detailed description is omitted here.

The collimated optical element 110 and the division optical element 120 are contained in one cylindrical container 150. In the container 150, the collimated optical element 110 and the division optical element 120 are arranged such that the light emission face 112 and the light incident face 121 are parallel and opposed to each other, and the optical axes of the both optical elements coincide with each other. At the end portion of the container 150, the detector 40 is attached. Thus, the distance from the light emission face 122 of the division optical element 120 to the light-receiving face 41 of the detector 40 is determined. In this example, the container 150 functions as the holding member of the present invention.

The components of the spectral measurement device 1C other than those described above are substantially the same as those of the spectral measurement device 1B of the third embodiment. Accordingly, the same or corresponding portions as those of the spectral measurement device 1B are given the same reference numerals, and a description is omitted.

According to the above configuration, when the object light generated at the measurement point SP of the sample S by light cast to the sample S from a light source not shown enters the light incident face 111 of the collimated optical element 110, the object light is converted into a parallel light beam and is emitted from the light emission face 112 of the collimated optical element 110. This parallel light beam travels straight through a space between the collimated optical element 110 and the division optical element 120 and enters the light incident face 121 of the division optical element 120. When refracted and emitted from each of the first light emission face 122A and the second light emission face 122B of the division optical element 120, each beam is divided into the first light beam and the second light beam, and enters the light-receiving face 41 of the detector 40 so that at least a part of each beam overlaps. Since there is an optical path length difference between the first light beam and the second light beam, an interference image of the first light beam and the second light beam is formed in a region where the first light beam and the second light beam overlap on the light-receiving face 41. Accordingly, it is obtained an interferogram of the measurement point SP by detecting the intensity distribution of light of this interference image by the detector 40, and it is obtained the spectral characteristics of the measurement point SP by Fourier-transforming the interferogram the processing unit 50.

Fifth Embodiment

Figure 21:
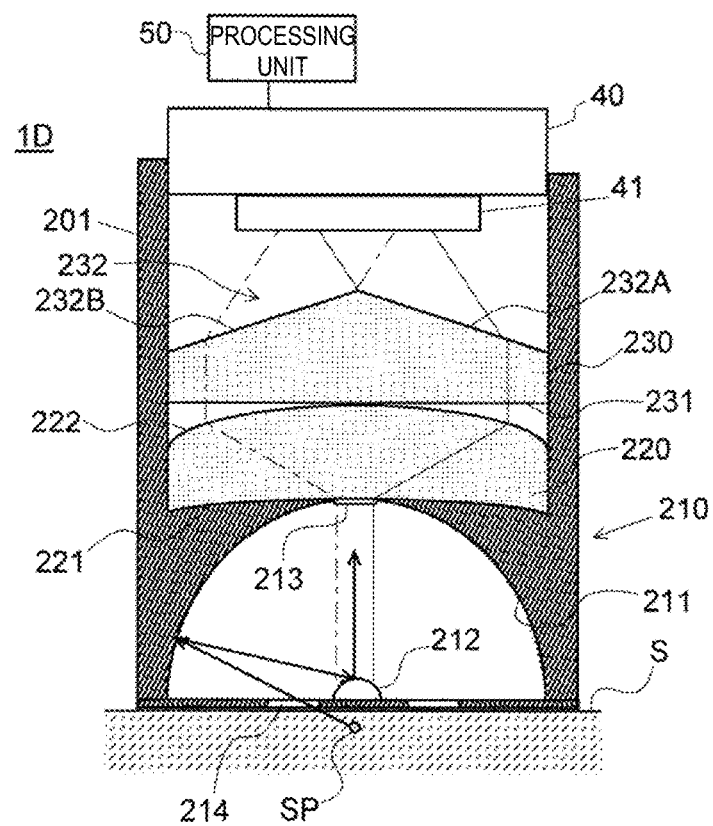
FIG. 21 is a schematic configuration view of a fifth embodiment of the spectral measurement device according to the present invention.

FIG. 21 is a schematic configuration view of the fifth embodiment of the spectral measurement device according to the present invention. In this spectral measurement device 1D, an interference optical system 200 includes a Cassegrain optical system 210 contained in a container 201 as a holding member, an enlargement optical element 220, and a division optical element 230. The container 201 is fixed to the detector 40.

The Cassegrain optical system 210 includes a main mirror 211, which is a concave mirror, and a sub mirror 212, which is a convex mirror. Both the main mirror 211 and the sub mirror 212 have a circular outer shape when viewed from above. The main mirror 211 is held in the container 201 with its concave face facing downward. The sub mirror 212 is arranged below the main mirror 211 with its convex face facing upward. The upper portion of the main mirror 211 and the bottom face of the container 201 are provided with an upper opening 213 and a lower opening 214 for passing light, respectively.

In a space above the main mirror 211 in the container 201, the enlargement optical element 220 and the division optical element 230 are held in order from the main mirror 211 side. The enlargement optical element 220 has a concave light incident face 221 and a convex light emission face 222, and the light incident face 221 is contained in the container 201 in close contact with the upper face of the main mirror 211. The division optical element 230 has a planar light incident face 231 and a convex light emission face 232. The shape of the division optical element 230 is the same as that of the division optical element 120 of the fourth embodiment, and the light emission face 232 includes a first light emission face 232A and a second light emission face 232B. The division optical element 230 is arranged in the container 201 such that its light incident face 231 comes into contact with the light emission face 222 of the enlargement optical element 220. The Cassegrain optical system 210, the enlargement optical element 220, and the division optical element 230 are contained in the container 201 in a state where their optical axes coincide with one another.

When acquiring the spectral characteristics of the sample S using the spectral measurement device 1D of the present embodiment, the spectral measurement device 1D is installed so that the bottom face of the container 201 comes into contact with the face of the sample S. In this state, when light from a light source not shown is cast to the sample S and object light is emitted in various directions from the measurement point SP in the sample S, some of the object light enter the container 201 from the lower opening 214, are combined into one parallel light beam through the main mirror 211 and the sub mirror 212, and then enter the light incident face 221 of the enlargement optical element 220 from the upper opening 213. The outer diameter of the parallel light beam incident on the light incident face 221 gradually increases when passing through the inside of the enlargement optical element 220, and it becomes a parallel light beam having an outer diameter larger than that when entered from the light incident face 221, and is emitted from the light emission face 222. Then, the parallel light beam emitted from the light emission face 222 enters the light incident face 231 of the division optical element 230, travels in the division optical element 230 toward the light emission face 232, is divided into the first light beam and the second light beam when refracted and emitted from the first light emission face 232A and the second light emission face 232B, respectively, and each light beam enters the light-receiving face 41 of the detector 40 in a state where at least a part of each light beam overlaps.

Accordingly, it is obtained an interferogram of the measurement point SP by detecting the intensity distribution of light of the region where the first light beam and the second light beam overlap (i.e., the interference image) on the light-receiving face 41 by the detector 40, and it is obtained the spectral characteristics of the measurement point SP by Fourier-transforming the interferogram the processing unit 50.

Next, some embodiments in which the spectral measurement device according to the present invention is applied to a spectral measurement unit will be described.

Sixth Embodiment

Figure 22:
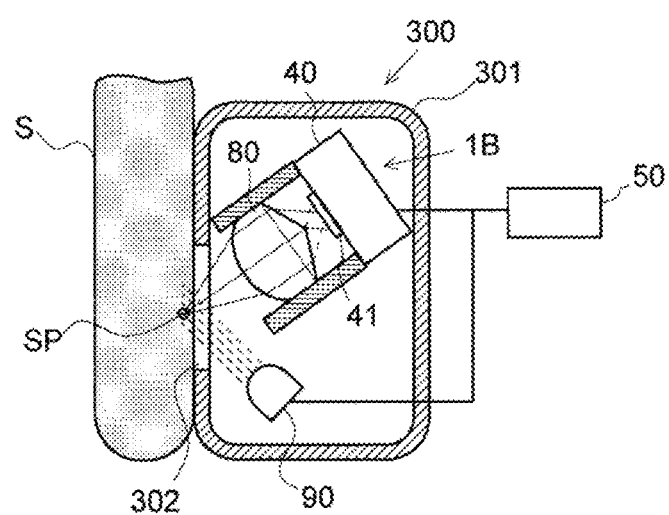
FIG. 22 is a schematic configuration view of a spectral measurement unit according to a sixth embodiment of the present invention.

A spectral measurement unit 300 shown in FIG. 22 has the spectral measurement device 1B, a light source 40, and a casing 301 which houses them. The casing 301 is attached with a window plate 302 made of a translucent member. Light from the light source 40 is emitted to the outside of the casing 301 through the window plate 302, and light from the outside enters the casing 301 through the window plate 302. The spectral measurement device 1B has the same configuration as that of the spectral measurement device 1B of the third embodiment described above, and the transmissive optical element 80 is arranged in the casing 301 so as to face the window plate 302 side.

In this spectral measurement unit 300, light from the light source 40 is caused to enter an object S to be measured from the window plate 302 in a state where the window plate 302 is brought into contact with the surface of the object S to be measured. Then, light emitted from the inside of the object S to be measured near the window plate 302 enters the casing 301 through the window plate 302, and the incident light is introduced into the spectral measurement device 1. At this time, when the light emitted from the focal point (This becomes the measurement point SP.) of the transmissive optical element 80 enters the transmissive optical element 80 of the spectral measurement device 1B, the incident light becomes a parallel light beam and is directed to the light emission face 82, is divided into the first light beam and the second light beam, and is emitted from the light emission face 82. The first light beam and the second light beam emitted from the light emission face 82 enter the light-receiving face 41 of the detector 40 in a partially overlapped state to form an interference image of the first light beam and the second light beam. Accordingly, the interferogram of the measurement point SP is obtained by measuring the intensity distribution of light of the interference image by the detector 40, and the spectral characteristics of the measurement point SP can be obtained by Fourier-transforming the interferogram by the processing unit 50.

Seventh Embodiment

Figure 23:
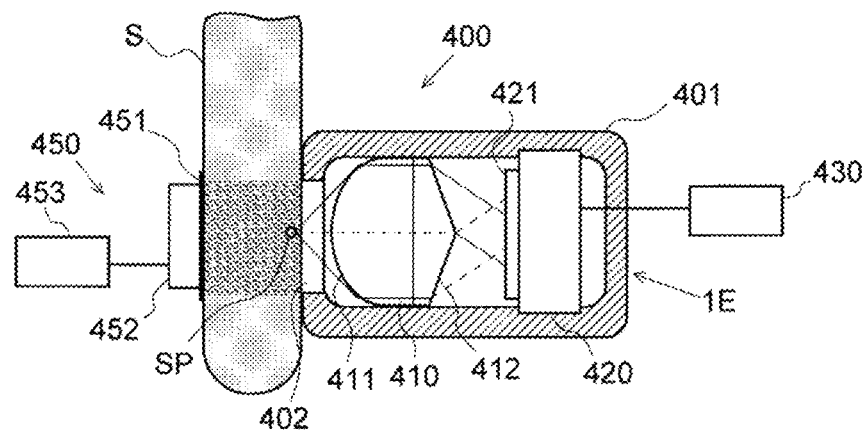
FIG. 23 is a schematic configuration view of a spectral measurement unit according to a seventh embodiment of the present invention.

As shown in FIG. 23, a spectral measurement unit 400 of this embodiment includes a cylindrical casing 401, a spectral measurement device 1E including a transmissive optical element 410 and a detector 420 contained in the cylindrical casing 401, and an ultrasonic heating device 450. The transmissive optical element 410 has the same configuration as that of the transmissive optical element 80 included in the spectral measurement device 1A of the second embodiment, and includes a light incident face 411 and a light emission face 412 including the first and second light emission faces. The detector 420 is connected with a processing device 430 via a signal line, and outputs a detection signal to the processing device 430. The casing 401 is attached with a window plate 402 made of a translucent member, and the window plate 402 and the light incident face 411 of the transmissive optical element 410 face each other, and the transmissive optical element 410 is arranged in the casing 401 so that the optical axis of the transmissive optical element 410 is orthogonal to the window plate 402.

The ultrasonic heating device 450 includes a plate material 451, an ultrasonic vibrator 452 attached to the plate material 451, and a drive device 453 which drives the ultrasonic vibrator 452.

A method of using the spectral measurement unit 400 will be described. Here, it is assumed that an object having a small thickness such as an earlobe is the object S to be measured.

First, the spectral measurement device 1E and the ultrasonic heating device 450 are arranged on both sides of the object S to be measured across the object S to be measured, the window plate 402 of the casing 401 is brought into contact with the surface of the object S to be measured, and the plate material 451 is brought into contact with the object S to be measured so as to face the window plate 402 across the object S to be measured.

In this state, when the drive device 453 is operated to supply alternating-current power to the ultrasonic vibrator 452, ultrasonic vibration is generated in a region (measurement region) between the plate material 451 and the window plate 402 of the object S to be measured, and the measurement region is ultrasonically heated. Thus, infrared rays are radiated from the measurement region, and the infrared rays pass through the window plate 402 and enter the transmissive optical element 410 in the casing 401. Among the infrared rays incident on the transmissive optical element 410, the infrared rays emitted from the measurement point SP, which is the focal point of the transmissive optical element 410, become parallel light beams and directed to the light emission face 412, and are divided into the first light beam and the second light beam and emitted from the light emission face 412. Then, the first light beam and the second light beam emitted from the light emission face 412 enter the light-receiving face 421 of the detector 420 in a partially overlapping state, and an interference image of the first light beam and the second light beam is formed. Accordingly, the interferogram at the measurement point SP is obtained by measuring the intensity distribution of light of the interference image by the detector 420, and the spectral characteristics of the measurement point SP can be obtained by Fourier-transforming the interferogram by the processing device 430.

In the spectral measurement unit 400, the spectral measurement device 1E and the ultrasonic heating device 450 functioning as a light source are separately provided. Accordingly, the spectral measurement device 1E can be smaller.

Eighth Embodiment

Figure 24:
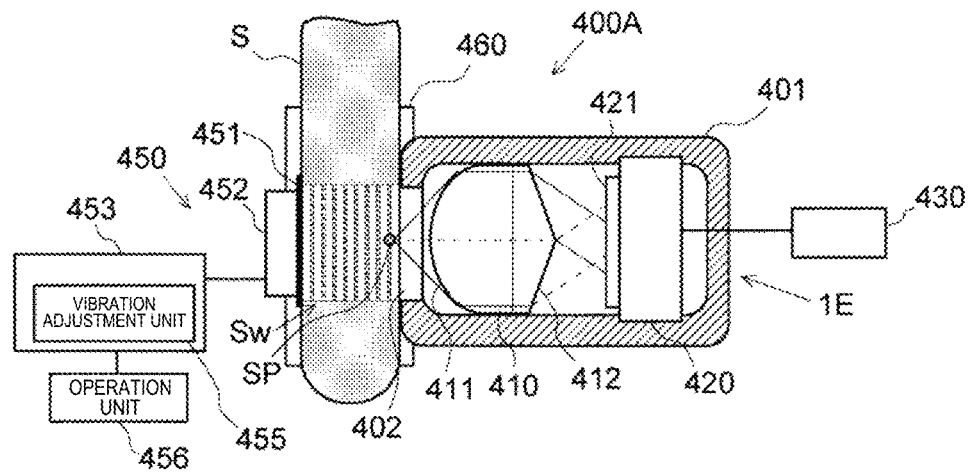
FIG. 24 is a schematic configuration view of a spectral measurement unit according to an eighth embodiment of the present invention.

As shown in FIG. 24, a spectral measurement unit 400A of this embodiment includes the spectral measurement device 1E, the ultrasonic heating device 450, and a mounting member 460 for mounting them onto the object S to be measured. The ultrasonic heating device 450 includes the plate material 451, the ultrasonic vibrator 452 attached to the plate material 451, the drive device 453 which drives the ultrasonic vibrator 452, a vibration adjustment unit 455 which adjusts the frequency of alternating-current power supplied by the drive device 453 to the ultrasonic vibrator 452 and the amplitude of ultrasonic vibration generated by the ultrasonic vibrator 452, and an operation unit 456 to be operated by a user. The mounting member 460 includes, for example, a clip, and the plate material 451, the ultrasonic vibrator 452, and the casing 401 are respectively attached on both end portions of the clip. When the mounting member 460 holds the object S to be measured, the plate material 451, the ultrasonic vibrator 452, and the casing 401 are fixed to the object S to be measured so that the plate material 451 and the window material 402 face each other across the object S to be measured.

Since the components of the spectral measurement unit 400A other than the above are the same as those of the spectral measurement unit 400 of the seventh embodiment, the same and corresponding parts are given the same reference numerals, and a description is omitted.

A method of using the spectral measurement unit 400A will be described. Also here, it is assumed that an object having a small thickness such as an earlobe is the object S to be measured.

First, the mounting member 460 holds the object S to be measured to fix the casing 401 of the spectral measurement device 1E and the plate material 451 and the ultrasonic vibrator 452 of the ultrasonic heating device 450 to both sides of the object S to be measured.

In this state, when the drive device 453 is operated to supply alternating-current power to the ultrasonic vibrator 452, ultrasonic vibration is generated in a measurement region between the plate material 451 and the window plate 402 of the object S to be measured, and the measurement region is ultrasonically heated. At this time, the operation unit 456 is operated to appropriately adjust the frequency of alternating-current power supplied to the ultrasonic vibrator 452 and the amplitude of ultrasonic vibration generated by the ultrasonic vibrator 452, an a standing wave which is orthogonal to the plate material 451 and has a node located at the measurement point SP is formed in the measurement region.

FIG. 24 schematically shows a scene in which a standing wave Sw is formed inside the object S to be measured. In the standing wave Sw, the energy is concentrated in the node part, and hence the node part is heated more strongly than the other parts and radiates infrared rays of high energy. When the standing wave Sw is formed so that a node is located at the measurement point SP, high-energy infrared rays are emitted from the measurement point SP, and the high-energy infrared rays enter the transmissive optical element 410 in the casing 401 through the window plate 402. The infrared rays from the measurement point SP incident on the transmissive optical element 410 become parallel light beams and directed to the light emission face 412, and are divided into the first light beam and the second light beam and emitted from the light emission face 412. The first light beam and the second light beam emitted from the light emission face 412 enter the light-receiving face 421 of the detector 420 in a partially overlapped state to form an interference image of the first light beam and the second light beam. Accordingly, the interferogram at the measurement point SP is obtained by measuring the intensity distribution of light of the interference image by the detector 420, and the spectral characteristics of the measurement point SP can be obtained by Fourier-transforming the interferogram by the processing device 430.

The standing wave Sw of ultrasonic vibration such that a node is located at the measurement point SP is formed, and infrared rays of high energy can be generated from the measurement point SP. Accordingly, it is possible to suppress the infrared rays radiated from the positions other than the measurement point SP, which do not contribute to the formation of the interference image on the light-receiving face 421 of the detector 420, to a small value, and hence it is possible to enhance the SN ratio.

Furthermore, by using the spectral measurement units 300, 400, and 400A of the above-described sixth to eighth embodiments, it is possible to easily measure the spectral characteristics of the object to be measured. In particular, the spectral measurement devices 1B and 1E incorporated in the spectral measurement units 300, 400, and 400A use the transmissive optical elements 80 and 410 in which the combining optical system and the phase shifter are integrated, and hence it is possible to reduce the size of the spectral measurement units 300, 400, and 400A. Accordingly, the spectral measurement units 300, 400, and 400A are suitable as a device that measures the spectral characteristics of, for example, blood flowing in a relatively small region such as an earlobe or a fingertip as an object to be measured, and that measures the biological component concentration such as glucose and cholesterol from the results.

The present invention is not limited to the examples described above, and appropriate modifications can be made.

The first embodiment is configured so that the optical axis of the object beam incident on the reflection face of the reference mirror 121 and the yz plane are parallel to each other, but the reference mirror 121 may be inclined slightly toward the inclined mirror 122. That is, the objective lens 10, the reference mirror 121, and the inclined mirror 122 may be arranged so that both the reference mirror 121 and the inclined mirror 122 are inclined to the optical axis side across the optical axis of the object beam.

The second embodiment is configured from the combining optical system, the phase shifter, and one optical element, but it is also possible to use separate optical elements.

The spectral measurement units 300 and 400 of the sixth embodiment and the seventh embodiment may include a mounting member for fixing the casing 301, the casing 401, and the ultrasonic heating device 450 to the object to be measured.

The spectral measurement device constituting the spectral measurement units 300, 400, and 400A may be the spectral measurement device 1 or 1A of the first or second embodiment, or may be the spectral measurement device 1D of the fifth embodiment.

In the spectral measurement device 1D of the fifth embodiment, the enlargement optical element is arranged between the Cassegrain optical system and the division optical element, but this enlargement optical element may be omitted.

REFERENCE SIGNS LIST 1, 1A, 1B, 1C, 1D, 1E . . . Spectral Measurement Device
10 . . . Objective Lens (Collimator Lens)
20 . . . Phase Shifter
21 . . . Reference Mirror (First Reflective Face)
22 . . . Inclined Mirror (Second Reflective Face)
40, 420 . . . Detector
41, 421 . . . Light-Receiving Face
50 . . . Processing Unit
80, 410 . . . Transmissive Optical Element
81 . . . Convex Face Portion
82 . . . Phase Shifter Portion
82A . . . First Transmission Portion
82B . . . Second Transmission Portion
110 . . . Collimated Optical Element (First Transmissive Optical Element)
120 . . . Division Optical Element (Second Transmissive Optical Element)
150, 201 . . . Container (Holding Member)
210 . . . Cassegrain Optical System
300, 400, 400A . . . Spectral Measurement Unit

The invention claimed is:

1. A spectral measurement device comprising:
a) a combining optical system configured to combine light emitted from a measurement point of an object to be measured into one single parallel light beam;
b) a detector having a light-receiving face and configured to detect an intensity distribution of light on the light-receiving face;
c) a phase shifter configured to divide a parallel light beam combined in the combining optical system into a first light beam and a second light beam, configured to emit the first light beam and the second light beam toward the light-receiving face while providing an optical path length difference between the first light beam and the second light beam, and configured to cause the first light beam and the second light beam to planarly enter the light-receiving face so that at least a part of an incident region of the first light beam on the light-receiving face and at least a part of an incident region of the second light beam overlap with each other; and
d) a processing unit configured to obtain an interferogram at the measurement point based on an intensity distribution of light in a region where an incident region of the first light beam and an incident region of the second light beam on the light-receiving face overlap, and configured to acquire a spectrum by Fourier-transforming the interferogram.

2. The spectral measurement device according to claim 1, wherein
the phase shifter has a first planar reflection face and a second planar reflection face arranged side by side so that the parallel light beam enters from an oblique direction, and
the first planar reflection face and the second planar reflection face are configured so that an incident angle of the parallel light beam with respect to the first planar reflection face and an incident angle of the parallel light beam with respect to the second planar reflection face are different from each other, and an incident face of the parallel light beam with respect to the first planar reflection face and an incident face of the parallel light beam with respect to the second planar reflection face are different from each other.

3. The spectral measurement device according to claim 2, wherein
the detector includes a two-dimensional area sensor, and
the processing unit sums up an intensity distribution of light by adding an intensity distribution of light detected on a line of the two-dimensional area sensor to an intensity distribution of light detected on another line by aligning an optical path length difference, and obtains an interferogram based on a summed up intensity distribution of light.

4. The spectral measurement device according to claim 1, wherein
the phase shifter includes a first transmission portion having a planar light-lead-in face and a planar light-lead-out face, and a second transmission portion having a planar light-lead-in face and a planar light-lead-out face, and is configured so that an optical axis of the second light beam emitted from the planar light-lead-out face of the second transmission portion is inclined with respect to an optical axis of the first light beam emitted from the planar light-lead-out face of the first transmission portion.

5. The spectral measurement device according to claim 4, wherein
a light-lead-in face and a light-lead-out face of the first transmission portion are parallel to each other,
a light-lead-out face is inclined with respect to a light-lead-in face of the second transmission portion, and
a light-lead-in face of the first transmission portion and a light-lead-in face of the second transmission portion are located on a same plane.

6. The spectral measurement device according to claim 5, wherein
the detector includes a two-dimensional area sensor, and
the processing unit sums up an intensity distribution of light by adding an intensity distribution of light detected on a line of the two-dimensional area sensor to an intensity distribution of light detected on another line by aligning an optical path length difference, and obtains an interferogram based on a summed up intensity distribution of light.

7. The spectral measurement device according to claim 4, wherein
the detector includes a two-dimensional area sensor, and
the processing unit sums up an intensity distribution of light by adding an intensity distribution of light detected on a line of the two-dimensional area sensor to an intensity distribution of light detected on another line by aligning an optical path length difference, and obtains an interferogram based on a summed up intensity distribution of light.

8. The spectral measurement device according to claim 1, wherein
the combining optical system includes a plate-shaped first transmissive optical element having a convex light incident face and a planar light emission face positioned on a back side of the convex light incident face,
the phase shifter includes a plate-shaped second transmissive optical element having a planar light incident face and a light emission face which is a face located on a back side of the planar light incident face and which includes two inclined faces having different inclinations from each other, and
the spectral measurement device further includes a holding member configured to integrally hold the first transmissive optical element and the second transmissive optical element so that their optical axes coincide with each other.

9. The spectral measurement device according to claim 8, wherein
the detector includes a two-dimensional area sensor, and
the processing unit sums up an intensity distribution of light by adding an intensity distribution of light detected on a line of the two-dimensional area sensor to an intensity distribution of light detected on another line by aligning an optical path length difference, and obtains an interferogram based on a summed up intensity distribution of light.

10. The spectral measurement device according to claim 1 comprising:
one transmissive optical element having a convex light incident face and a light emission face which is a face located on a back side of the convex light incident face and includes two inclined faces having different inclinations from each other, wherein
a part of the transmissive optical element from the convex light incident face to the light emission face functions as the combining optical system, and the two inclined faces constituting the light emission face function as the phase shifter.

11. The spectral measurement device according to claim 10, wherein
the detector includes a two-dimensional area sensor, and
the processing unit sums up an intensity distribution of light by adding an intensity distribution of light detected on a line of the two-dimensional area sensor to an intensity distribution of light detected on another line by aligning an optical path length difference, and obtains an interferogram based on a summed up intensity distribution of light.

12. The spectral measurement device according to claim 1, wherein
the combining optical system includes a Cassegrain optical system including a convex mirror and a concave mirror,
the phase shifter includes a plate-shaped transmissive optical element having a planar light incident face and a light emission face which is a face located on a back side of the planar light incident face and which includes two inclined faces having different inclinations from each other, and
the spectral measurement device further includes a holding member configured to integrally hold the Cassegrain optical system and the transmissive optical element so that their optical axes coincide with each other.

13. The spectral measurement device according to claim 12, wherein
the detector includes a two-dimensional area sensor, and
the processing unit sums up an intensity distribution of light by adding an intensity distribution of light detected on a line of the two-dimensional area sensor to an intensity distribution of light detected on another line by aligning an optical path length difference, and obtains an interferogram based on a summed up intensity distribution of light.

14. The spectral measurement device according to claim 1, wherein
the detector includes a two-dimensional area sensor, and
the processing unit sums up an intensity distribution of light by adding an intensity distribution of light detected on a line of the two-dimensional area sensor to an intensity distribution of light detected on another line by aligning an optical path length difference, and obtains an interferogram based on a summed up intensity distribution of light.

15. A spectral measurement method comprising:
a) combining light emitted from a measurement point of an object to be measured into one parallel light beam by means of a combining optical system;
b) dividing, by a phase shifter, a parallel light beam emitted from the combining optical system into a first light beam and a second light beam, emitting the first light beam and the second light beam toward a light-receiving face of a detector while providing an optical path length difference between the first light beam and the second light beam, and causing the first light beam and the second light beam to planarly enter the light-receiving face so that at least a part of an incident region of the first light beam on the light-receiving face and at least a part of an incident region of the second light beam overlap with each other; and
c) obtaining an interferogram at the measurement point based on an intensity distribution of light in a region where an incident region of the first light beam and an incident region of the second light beam on the light-receiving face overlap, and acquiring a spectrum by Fourier-transforming the interferogram.

16. A transmissive optical element comprising:

a convex light incident face; and a light emission face located on a back side of the convex light incident face and including two inclined faces having different inclinations from each other, wherein a light incident on the convex light incident face from a focal point of the convex light incident face is converted into a parallel light beam, the parallel light beam is divided into a first light beam and a second light beam, and an optical path length difference is provided between the first light beam and the second light beam, and the first light beam and the second light beam are emitted from the light emission face so that the first light beam and the second light beam overlap each other at least in a part on a face located at a predetermined distance from the light emission face.

\* \* \* \* \*